(12) United States Patent
Kester et al.

(10) Patent No.: US 6,339,222 B1
(45) Date of Patent: Jan. 15, 2002

(54) DETERMINATION OF IONIC SPECIES CONCENTRATION BY NEAR INFRARED SPECTROSCOPY

(75) Inventors: Michael Kester, Richmond; Denys F. Leclerc; Thanh P. Trung, both of Vancouver; Edward A. Dylke, Prince George, all of (CA)

(73) Assignees: Kvaerner Canada Inc., Vancouver; Pulp & Paper Research Institute of Canada, Pointe-Claire, both of (CA)

( * ) Notice: Subject to any disclaimer, the term of this patent is extended or adjusted under 35 U.S.C. 154(b) by 0 days.

(21) Appl. No.: 09/314,885

(22) Filed: May 19, 1999

Related U.S. Application Data

(63) Continuation-in-part of application No. 09/190,850, filed on Nov. 12, 1998.

(51) Int. Cl.$^7$ ................................................. D21C 7/14

(52) U.S. Cl. ..................................... 250/339.09; 162/49

(58) Field of Search ..................... 250/339.09, 339.05; 162/49

(56) References Cited

U.S. PATENT DOCUMENTS

| | | | |
|---|---|---|---|
| 3,553,075 A | | 1/1971 | Rivers |
| 3,607,083 A | | 9/1971 | Chowdhry |
| 3,886,034 A | | 5/1975 | Noreus |
| 4,024,229 A | | 5/1977 | Smith et al. |
| 4,743,339 A | * | 5/1988 | Faix et al. .................... 162/49 |
| 5,082,516 A | | 1/1992 | Dorris |
| 5,104,485 A | * | 4/1992 | Weyer ......................... 162/49 |
| 5,282,931 A | * | 2/1994 | Leclerc ........................ 162/49 |
| 5,364,502 A | | 11/1994 | Leclerc et al. |
| 5,378,320 A | | 1/1995 | Leclerc et al. |
| 5,536,942 A | * | 7/1996 | Barringer et al. ...... 250/339.12 |
| 5,582,684 A | | 12/1996 | Holmquist et al. |
| 5,616,214 A | * | 4/1997 | Leclerc ........................ 162/49 |

FOREIGN PATENT DOCUMENTS

| | | | |
|---|---|---|---|
| WO | WO 91/17305 | 11/1991 | |
| WO | WO-98/10137 A1 | * 3/1998 | ........... D21C/11/00 |

OTHER PUBLICATIONS

Lin et al. "Near–IR . . . Solution", Anal. Chem. 1993, vol. 65, pp. 287–292.*
Baptista et al. "Near–Infrared detection . . . Spectrophotometry", Anal. Chem. 1996, vol. 68, pp. 971–976.*
Phelan et al. "Measurement . . . 700–1150 nm", Anal. Chem. 1989, vol. 61, pp. 1419–1424.*

(List continued on next page.)

Primary Examiner—Constantine Hannaher
Assistant Examiner—Otilia Gabor
(74) Attorney, Agent, or Firm—Pillsbury Winthrop LLP

(57) ABSTRACT

A method for determining the concentration of hydrogen ion, organic anionic species and anionic species selected from the group consisting of $OH^-$, $CO_3^=$, $HS^-$, $ClO_3^-$, $SO_4^=$, $S_2O_3^=$, polysulphide and peroxide in an aqueous sample solution, said method comprising subjecting said solution to near infrared radiation at a wavelength region of wave numbers selected from about 7,000 to 14,000 cm$^{-1}$ through a solution path length of at least 3 mm to obtain spectral data for said solution; obtaining comparative spectral data for said anionic species at known concentrations in aqueous solutions; and correlating by multivariate calibration the relationships between said spectral data of said sample solution and said comparative spectral data to determine said concentration of said anionic species in said sample solution. The method is of particular value for use with pulp liquor determination and control in regards to the rapid and accurate determination of the $OH^-$, $HS^-$, $CO_3^=$, $ClO_3^-$, $SO_4^=$, $S_2O_3^=$, polysulphide and peroxide anionic species, hydrogen cation and of organic species present in pulp liquor.

25 Claims, 30 Drawing Sheets

OTHER PUBLICATIONS grant et al. "Simultaneous determination . . . Spectrometry", Analyst, 1989, vol. 114, pp. 819–822.*

Molt et al. "Analysis . . . with strong bases", Journal of molecular Structure 410–411, 1997, pp. 565–572.*

Wiedemann et al. "Developing . . . esters", NIR 1997, pp. 149–156.*

Peters "Stretching and bending . . . Software", SPIE vol. 2367, pp. 146–158.*

Czarnecki et al. "Potential . . . Liquid phase", Applied Spectroscopy 1993, vol. 47, pp. 2162–2168.*

Stark "Near–infrared Spectroscopy", SPIE 1991, vol. 1575, pp. 70–86.*

Mackison et al. "A Demonstration . . . Analysis", Applied Spectroscopy 1992, vol. 46, pp. 1020–1024.*

Hyvarinen et al. "Rugged . . . measurements", SPIE 1990, vol. 1266, pp. 99–104.*

Vanchinithan et al. "Kraft–liquor . . . spectroscopy", Tappi Journal, vol. 79, pp. 187–191.*

Patrick "new online green . . . costs", Pulp & Paper, 1998, pp. 39–47.*

Haegglund, Svensk Papperstidn, 49(9):191, 1946.

Green, Chemical Recovery in the Alkalinen Pulping Process, Tappi Press, pp. 257–268, 1985.

Danielsson et al, Journal of Pulp and Paper Science, 22(6), 1996.

Vroom, Pulp Paper Mag Can., 58(3):228, 1957.

Peramunage et al, Anal. Chem., 66:378–383, 1994.

Paulonis et al, J. Pulp Paper Sci., 20(9):J254–J258, 1994.

Salomon et al, J. Chromatogr., 601(1–2):219–25, 1992.

Rapid Ion Monitoring of Kraft Process Liquors by Capillary Electrophoresis, Process Control Qual., 3(1–4):219–271, 1992.

Mitchell, Tappi J., 73(4):235, 1990.

Leclerc et al, J. Pulp Paper Sci., 21(7):231, 1995.

Haaland et al, Anal. Chem., 60(10):1193–1202, 1988.

Haaland et al, Anal. Chem., 60 (10):1202–1208, 1988.

Lin et al, Appl. Spectrosc., 46(12):1809–15, 1992.

Lin et al, Environ. Sci. Technol., 27(8):1611–6, 1993.

Lin et al, Anal. Chem., 65(3):287–92, 1933.

Lin et al, Appl. Spectrosc., 47(1):62–8, 1993.

Lin et al, Appl. Spectrosc., 47(2):239–41, 1993.

Watson et al, Spectroscopy, 2(1):44, 1987.

Hirschfeld, Appl. Spectrosc., 39(4):740–1, 1985.

Grant et al, Analyst., 114(7):819–22, 1989.

Vanchinathan, Tappi J., 79(10):187–191, 1996.

Phelan et al, Anal. Chem., 61(3):1419–24, 1989.

Binette et al, Proc. Int. Conf., Near Infrared Spectrosc. 7th, 287–289, 1996.

* cited by examiner

DETERMINATION OF IONIC SPECIES CONCENTRATION BY NEAR INFRARED SPECTROSCOPY

RELATED APPLICATION

This is a continuation-in-part application of Ser. No. 09/190,850, filed Nov. 12, 1998.

FIELD OF THE INVENTION

This invention relates generally to a method for determining ionic species, particularly anionic species in aqueous solution, particularly pulp process liquors of cellulosic pulp manufacturing processes, by near infrared spectrophotometry and more particularly to the use of an on-line method for determining concentration parameters of said process liquors, and subsequent control of said cellulosic pulp manufacturing process by use of said determined parameters.

BACKGROUND OF THE INVENTION

Kraft pulping is performed by cooking wood chips in a highly alkaline liquor which selectively dissolves lignin and releases the cellulosic fibers from their wooden matrix. The two major active chemicals in the liquor are sodium hydroxide and sodium sulfide. Sodium sulfide, which is a strong alkali, readily hydrolyses in water to produce one mole of sodium hydroxide for each mole of sodium sulfide. The term "sulfidity" is the amount of sodium sulfide in solution, divided by the total amount of sodium sulfide and sodium hydroxide and is usually expressed as a percentage (% S) which varies between 20 and 30 percent in typical pulping liquors. The total amount of sodium hydroxide in solution, which includes the sodium hydroxide produced as the hydrolysis product of sodium sulfide, is called either "effective alkali" (EA), expressed as sodium oxide, $Na_2O$ before pulping, or residual effective alkali (REA) after pulping. Timely knowledge of these parameters would enable good control of the pulping process.

At the beginning of the kraft process, "white liquor" is fed to a digester. This white liquor contains a high amount of effective alkali up to 90 g/L, as $Na_2O$. At intermediate points in the digester, spent liquor, or "black liquor," is extracted from the digester. This spent liquor contains low levels of effective alkali—less than 30 g/L, as $Na_2O$ and also contains large amounts of organic compounds which, generally, are burned in a recovery furnace. Resultant inorganic residue, called smelt, is then dissolved to form "green liquor" which has a low concentration of effective alkali and a high concentration of sodium carbonate—up to 80 g/L, as $Na_2O$. White liquor is regenerated from the green liquor by causticizing the carbonate through the addition of lime. After the recausticizing operation, a small residual amount of sodium carbonate is left in the white liquor. The combined amount of sodium hydroxide, sodium sulfide and sodium carbonate is called total titratable alkali (TTA). The causticizing efficiency (CE) is usually defined as the difference in the amounts, as $Na_2O$ of sodium hydroxide between the white and green liquors, divided by the amount, as $Na_2O$ of sodium carbonate in the green liquor. Sodium sulfate, sodium carbonate and sodium chloride represent a dead load in the liquor recycling system. The reduction efficiency (RE) is defined as the amount, as $Na_2O$ of green-liquor sodium sulfide, divided by the combined amounts, as $Na_2O$, of sodium sulfide, sodium sulfate, sodium thiosulfate and sodium sulfite in either green liquor or the smelt.

The timely knowledge of the white-liquor charge of EA and of black-liquor EA would close the control loop in the digester and optimise for example, production and product quality and chemical utilization, of alkali and lime consumption. The control of sodium sulfide, TTA and of non-process electrolytes, such as sodium chloride and potassium chloride would also have a beneficial impact on closed-cycle kraft-mill operations. For example, environmentally-driven reduction of sulfur losses generally increases liquor sulfidity, thereby creating a sodium:sulfur imbalance that needs to be made up through the addition of caustic soda. Another important need is the control of TTA in green liquor, which is most easily done by adding weak wash to a smelt dissolving tank. The value of the green-liquor TTA is important because it is desirable to maintain the TTA at an optimal and stable level so as to avoid excess scaling while obtaining a high and stable white liquor strength. The ongoing development of modern chemical pulping processes has thus underscored the need for better control over all aspects of kraft-mill operations and more efficient use of all the chemicals involved in the process by knowledge of the concentration of aforesaid species in the liquors.

Sodium carbonate is difficult to characterise and quantify in situ because of a current lack of on-line sensors which can tolerate long-term immersion in highly alkaline liquors. Important economic benefits could result from causticizing control with a reliable sensor for sodium carbonate. Accurate causticization is critical for the uniform production of high-strength white liquor in that adding too much lime to the green liquor produces a liquor with poorly settling lime mud, whereas adding too little produces a liquor of weak strength. Determining the relative quantities of EA and carbonate in green and white liquor is thus important for controlling the causticizing process.

The recovery furnace of a recovery process produces a molten salt (smelt) that contains, in part, oxidized and reduced sulfur compounds. This smelt is dissolved in water to produce raw green liquor. The oxidized sulfur compounds are mainly in the form of sodium thiosulphate ($Na_2S_2O_3$) and sodium sulfate ($Na_2SO_4$), while the reduced sulfur is in the form of sodium sulphide ($Na_2S$). Since only the sodium sulphide is useful in the pulping process, it is desirable to keep the proportion of sulfur that is reduced, known as the reduction efficiency, as high as possible. Timely measurement of sulphate and thiosulphate in the raw green liquor would allow improved control of the recovery boiler's reduction efficiency.

Some mills produce fully oxidized white liquor for use in the bleach plant. In this process, the sodium sulphide ions in the white liquor are first partially oxidized to sodium thiosulphate ($Na_2S_2O_3$), and then filly oxidized to sodium sulfate ($Na_2SO_4$). Timely measurement of the sodium thiosulphate concentration that is remaining in the liquor would allow improved control of the oxidation process.

It is known that an increase in carbohydrate yield in a kraft cook can be achieved by the addition of sodium polysulphide to conventional white liquor. Reference is made to this process in an article published in *Svensk Papperstidn*, 49(9):191, 1946 by E. Haegglund. Sodium polysulphide acts as a stabilizing agent of carbohydrates towards alkaline peeling reactions. Thus, polysulphide-cooking results in a significant pulp yield gain, which provides increased pulp production, and reduces the cost of wood chips.

A common method for producing polysulphide is to convert the sodium sulphide already present in the white liquor to polysulphide by an oxidation process. Several variants of this method are reported by Green, R. P. in

*Chemical Recovery in the Alkaline Pulping Process*, Tappi Press, pp. 257 to 268, 1985 and by Smith, G. C. and Sanders, F. W. in the U.S. Pat. No. 4,024,229. These procedures generally involve redox and catalytic or electrochemical processes.

A typical polysulphide process is carried out in the recausticizing tank, which has a residence time of approximately 60 minutes. An example of such a process is described in G. Dorris U.S. Pat. No. 5,082,526. The main product, polysulphide, is produced through an oxidation reaction which also creates sodium thiosulphate through over-oxidation. Process conditions must therefore be controlled so that a maximal amount of polysulphide is produced. With a closed-loop control system, this is best achieved with a minimum sampling rate of 4 samples per unit of residence time. The traditional methods presently available for polysulphide are based on wet chemical methods and all take several hours. Therefore, they are not suitable for control methods. A spectrophotometric method had been reported by Danielsson et. al, *Journal of Pulp and Paper Science*, 22(6), 1996. Unfortunately, this method must either use a short pathlength, on the order of 50 $\mu$m, or use diluted liquors, both of which are not practical for online applications. A method that does not require dilution is desirable.

Traditionally, hydrogen peroxide has been used in chemical pulp bleaching for providing marginal increases in brightness near the end of the bleaching process. More recently, the use of hydrogen peroxide as a bleaching agent for kraft pulp has been growing rapidly because of the elimination of elemental chlorine from the chlorination stage and the implementation of oxygen delignification. The use of peroxide reinforces the oxidative extraction stage by delignifying as well as bleaching the pulp in the EOP stage, and enables the preceding chlorine dioxide stage (D) to be run at a much lower chlorine dioxide charge, thereby preventing the formation of environmentally harmful by-products such as dioxins. This practice also allows the mill to maintain its final brightness target.

Peroxide bleaching is strongly affected by pH, which must be adjusted and buffered at around 10.5 for best results. The pH of the bleach liquor is usually controlled by the addition of sodium hydroxide. A chelating agent such as di-ethylene-tetra-amine-penta-acetic acid (DTPA) or sodium silicate is also added, which act both as a stabilizer and as a buffering agent in the peroxide bleaching system. DTPA scavenges trace transition metals, such as manganese, which decompose hydrogen peroxide. Magnesium sulfate is added as a final stabilizing agent during the pulp-bleaching step. Since hydrogen peroxide is an expensive chemical, its concentration in the bleach liquor (typically between three to five percent by volume) must be carefully controlled so as to yield maximal benefit from its use.

Chlorine dioxide solution ($ClO_{2(aq)}$) is a bleaching agent commonly used in the production of chemical pulps. Chlorine dioxide is generated by reacting sodium chlorate ($NaClO_3$) with a reducing agent, typically liquid methanol ($CH_3OH$) or sulfur dioxide ($SO_2$) gas. A strong acid, typically sulfuric acid ($H_2SO_4$) or hydrochloric acid (HCl), is normally present to increase the reaction rate.

Efficient production of chlorine dioxide requires that the chlorate and acid concentration in the generator be kept at optimum levels. If the either the chlorate or acid concentration varies, undesirable chemical reactions occur that reduce generator efficiency. Timely knowledge of the chlorate and acid concentrations in the generator and in the feed streams would allow improved control of the chlorine dioxide generator.

Current control technology for chlorine dioxide generation from chlorate and sulphuric acid consists of regularly monitoring the generated chlorine dioxide by UV spectrometry, and using the results for feedback control of the process. However, chlorate and sulphuric acid are only very sporadically measured in the laboratory by titration, thereby leading to untimely and incomplete feed-forward control of the generating process. Titration is currently the method of choice, since the generating liquor contains a high level of bubbles and solids such as sesquisulphate, and is generally thought not to be suitable for on-line spectrometric analysis.

The choice of infrared-transparent optical materials for use in this application is rather limited. Only diamond and fused silica can withstand strongly acidic liquors. In the mid-infrared, a short pathlength must be used because of strong absorption by the fundamental bands of water. Normally, ATR would be the technique of choice because of the short pathlength and the strong fundamental bands for chlorate. However, silica cannot be used since it is opaque below 2200 $cm^{-1}$. Also, diamond is susceptible to scaling, and strongly absorbs in the region used for monitoring sulfate and chlorate if more than two reflections are used, which makes it unsuitable for quantitative analysis due to the lack of precision with the absorbance measurements.

On the other hand, in the near-infrared region, one can use a transmission cell with a relatively long pathlength. This pathlength should be long enough to permit adequate determination of the analyte for process control purposes. The presence of bubbles and solids would discourage a person ordinarily skilled in the art of $ClO_2$ generation from investigating the relatively long pathlength needed for a successful application.

Contrary to expectations, we have found that a near-infrared on-line spectrometric method is indeed possible for the analysis of chlorate and sulfuric acid. This method enables mill personnel to implement effective feed-forward control and to safely operate the generator under optimal conditions.

Various methods of on-line measurements of either EA or sodium hydroxide have been proposed. The use of conductivity methods for green and white liquors is well-established as a pulp and paper technology. Unfortunately, conductivity probes are prone to drift due to scaling, as well as interferences from other ionic species. Therefore, these devices require frequent maintenance and re-calibration. An early example of such measurements describes a method that can determine the EA by neutralizing hydroxide ions with carbon dioxide (1). The conductivity of the solution is measured before and after treatment. The difference in conductivities is proportional to the hydroxide ion concentration of the liquor. High levels of sodium hydroxide, however, will increase the neutralizing time. In white liquors, this time is too long for effective process control purposes. Chowdhry (2) describes an analysis of kraft liquors that uses differences in conductivity before and after precipitation of carbonates using $BaCl_2$, an approach which is not practical.

However, even though conductivity probes may not be suitable for on-line measurements of EA in white or green liquors, this kind of sensor is also used with the liquor produced during the early stages of the pulping in upper-recirculation digester lines. An example of a successful commercial version of an automatic titrator (3) involves titrating alkali with sulfuric acid until no change in conductivity is observed. This determination is straightforward and works very well for the impregnation and early stages of the cook, but not for the extraction stage. With extraction liquors, a more complex pattern is observed when significant quantities of organic acids and black-liquor solids appear in the liquor, and the end-point determination becomes more difficult near the end of the cook. On-line titration methods used in pulp mills suffer from frequent maintenance problems. Thus, most mill-site measurements still rely on standard laboratory methods.

At present, control of digesters is performed by keeping the chip and white liquor feeds at preset levels. These levels are determined by the overall production rate, and control is achieved by adjusting the temperature profile of the cook and determining the resultant blow-line kappa number. The philosophy behind this strategy is that alkali consumption during the removal of lignin is proportional to chip feed at a given kappa number. Alkali not consumed in the impregnation phase is then available for the bulk removal of lignin that occurs in the pulping zone. This is usually performed by predicting the pulp yield with the H-factor (4). The disadvantage of this method is that it assumes uniform chip moisture content, pH and density, as well as digester temperature, etc. Since the pulp must be analysed in the laboratory for lignin content, this makes it difficult to close the control loop in a timely manner. Ideally, a much better way of controlling digester operations would be to measure the EA concentration in black liquor directly on-line at an appropriate time in the cooking process on both the upper and lower (main) recirculation loops in the digester, as well as the REA concentration on the extraction line at the end of the cook. An on-line method that would give a direct measurement of the EA throughout a cook is therefore needed.

Methods relying on spectroscopic methods have been proposed because of the limitations of titration and conductivity methods for liquor analysis. It is known that hydrosulfide ions absorb very strongly in the ultraviolet at 214 nm (5, 6, 7). However, this absorption is so strong that a very small pathlength, i.e. less than 10 microns is needed to get a measurable signal which yields a linear calibration curve (8). A cell with such a small optical path is prone to plugging and, hence, not practical for on-line applications. Extensive $1:1\times10^3$ or $10^4$ dilution is practiced, which results in inaccurate results and increases the risk of sulfide being oxidized.

The dilution approach has also been used in techniques such as capillary zone electrophoresis which use UV detectors (9, 10). Errors in sulfidity measurements exceeding 50% were reported. Accordingly, a method which does not need dilution is needed.

Infrared spectroscopy can distinguish between the inorganic and organic components of liquors and a number of infrared methods have been proposed. Faix et al (11) propose a method for organic compounds in black liquor, based upon on-line infrared attenuated reflectance (ATR) measurements between 1400 and 1550 $cm^{-1}$. A similar method for kappa number determination (12) correlates the increase in the integrated band intensity at 1118 $cm^{-1}$ with decreasing kappa number. Neither of these methods can be used for process control because of interferences from carbohydrates and uncertainties in the value of process variables such as liquor-to-wood ratio. Leclerc et al. (13, 14, 15, 16) teach that one can measure EA and dead-load components in kraft liquors with FT-IR ATR, and that one can use these measurements to control the operations of important process units involved in the manufacture of kraft pulp such as the digester, recausticizers and recovery boiler. However, ATR optical reflecting elements immersed in very alkaline liquors, and/or acidic or oxidizing cleaning solutions, are prone to be vulnerable to etching and/or scaling of their surface, which necessitates frequent replacement, re-polishing and re-calibration of the elements. Materials that are resistant to caustic, acidic, or oxidizing environments are few and cannot be used for ATR measurements in the mid-infrared region of interest due to infrared absorption of the material itself. ATR elements have also slightly differing optical paths and surface properties that exhibit memory, which makes the transfer to other instruments of calibrations developed on one instrument very difficult to achieve without substantial expenditures of time and labour.

Recent advances in FT-IR instrumentation and software have made possible the more widespread use of the near-infrared region of the spectrum for deterinig aqueous components such as dissolved electrolytes. Each ionic species causes a unique and measurable modification to the water bands that is proportional to its concentration. Advantages over previous techniques include: no sample preparation, short measurement times, relatively long optical paths and the possibility of using fiber-optic technology for real-time, in situ measurements. Also, temperature effects and interferences by other cations and anions can be modeled in this spectral region through the use of partial least-squares (PLS) multi-component calibration techniques. PLS is a well-known multi-component calibration method (17, 18). This method enables one to build a spectral model which assumes that the absorbance produced by a species is linearly proportional to its concentration. This has been shown by (19, 20, 21, 22, 23). However, because of its relatively intense water bands, the spectral region situated from 4000 to 8000 $cm^{-1}$ is only suitable for optical paths ranging from 0.5 to 1.5 mm, a limitation which precludes the accurate determination of weakly absorbing electrolytes such as carbonate, sulfide and chloride. Sodium hydroxide, on the other hand, generates a strong signal that is easily detectable in this region (24, 25, 26). The concentration of dissolved electrolytes, such as sodium hydroxide, carbonate and chloride concentrations in aqueous streams, such as seawater or white liquor have been measured. Accurate results were obtained for hydroxide but not for the other ions. Similar results were obtained more recently (27) with a PLS calibration. The correlation data obtained for sulfide and carbonate are not reliable, and cannot be used as a basis towards developing a method for controlling the manufacture of cellulosic pulp. A near-infrared PLS method, which can measure sodium sulfide and TTA with an accuracy of 1 to 2 g/L has been described (28). The calibration method, however, could not distinguish between sodium carbonate and sodium hydroxide because of the similar spectral signatures produced by these two ions, as well as the relative weakness of the carbonate spectrum. Reference 24 through 28 demonstrate that hydroxide is easy to measure in the range 4000 to 8000 $cm^{-1}$, while other components such as carbonate and sulphide are not. The results obtained (27, 28) strongly suggest that a control method for a pulp manufacturing process based on the simultaneous and separate determination of hydroxide, carbonate and sulfide would be very difficult with the small-bore flow cell used for their work. This type of flow cell would also be susceptible to plugging by suspended solids and fibers, thereby rendering the method unworkable. The spectral region situated from 8000 to 12000 $cm^{-1}$ is more amenable to the use of longer optical paths ranging from 3 to 20 mm, which makes it much easier to couple a wide-bore flow cell to any system of pipes used in the mill. For example, (23, 29) a PLS calibration has been used to resolve the hydroxide and chloride ion spectrum near 10500 cm$^{-1}$. In both cases, however, the range of concentration was extremely wide (0 to 5 moles/L), the spectra were somewhat noisy, and the precision was no better than 5 g/L for both species. For the spectral information to be useful for process control engineers, the correlation data must be accurate to within one percent and the level of precision, in the range of 0.5 to 1 g/L. The level of precision reported is, thus, inadequate for process control.

A recent publication (30) broadly discloses a method of controlling the causticizing reaction for producing a white liquor having multiple white liquor components from a green liquor having multiple green liquor components, comprising the steps of measuring a characteristic of each of said green liquor components; measuring a characteristic of each of said white liquor components; evaluating said green liquor component characteristics and said white liquor component characteristics in a non-linear, application adaptable controller to produce a causticizing control signal; and controlling said causticizing reaction responsive to said causticization control signal to produce white liquor wherein the characteristics are generally measured by near infrared or polarographic measurement devices and evaluating the characteristics in a non-linear, application adaptable controller to produce a causticizing control signal for controlling the amount of time to a shaker. However, the specific multiple component liquid process analyzer of use in the disclosed process would require a pathlength of less than 3 mm at 1100 to 2200 nm to avoid complete saturation of the incident light beam by water molecules in the sample.

There is, therefore, a need for the rapid determination of effective alkali, residual alkali, sodium sulfide and sodium carbonate, particularly, in pulping process liquor by spectrophotometric means which provide for a process liquor pathlength of greater than 3 mm without saturation of the incident radiation beam by water molecules of the sample.

LIST OF PUBLICATIONS

1. U.S. Pat. No. 3,553,075—Rivers
2. U.S. Pat. No. 3,607,083—Chowdhry
3. U.S. Pat. No. 3,886,034—Noreus
4. K. E. Vroom, Pulp Paper Mag.Can., 1957, 58(3), 228
5. U.S. Pat. No. 5,582,684—Holmquist and Jonsson
6. D. Peramunage, F. Forouzan, S. Litch. Anal. Chem., 1994, 66, 378–383
7. Paulonis et al. PCT Application WO 91/17305. Liquid Composition Analyser and Method
8. Paulonis et Krishnagopalan. Kraft White and Green Liquor Composition Analysis. Part I: Discrete Sample Analyser. J. Pulp Paper Sci., 1994, 20(9), J254–J258
9. Salomon, D. R., Romano, J. P. Applications of Capillary Ion Analysis in the Pulp and Paper Industry. J. Chromatogr., 1992, 602(1–2), 219–25
10. Rapid Ion Monitoring of Kraft Process Liquors by Capillary Electrophoresis. Process Control Qual., 1992, 3(1–4), 219–271.
11. U.S. Pat. No. 4,743,339. Faix et al.
12. Michell. Tappi J., 1990, 73(4), 235.
13. Leclerc et al. J. Pulp Paper Sci., 1995, 21(7), 231
14. U.S. Pat. No. 5,282,931—Leclerc et al.
15. U.S. Pat. No. 5,364,502—Leclerc et al.
16. U.S. Pat. No. 5,378,320—Leclerc et al.
17. Haaland, D. M. and Thomas, E. V. Anal. Chem., 60(10): 1193–1202 (1988)
18. Haaland, D. M. and Thomas, E. V. Anal. Chem., 60(10): 1202–1208 (1988)
19. Lin and Brown. Appl. Spectrosc. 1992, 46(12), 1809–15
20. Lin and Brown. Environ. Sci. Technol. 1993, 27(8), 1611–6
21. Lin and Brown. Anal. Chem., 1933, 65(3), 287–92
22. Lin and Brown. Appl. Spectrosc. 1993, 47(1), 62–8
23. Lin and Brown. Appl. Spectrosc. 1993, 47(2), 239–41
24. Watson and Baughman. Spectroscopy, 1987, 2(1), 44
25. Hirschfeld. Appl. Spectrosc., 1985, 39(4), 740–1
26. Grant et al. Analyst., 1989, 114(7), 819–22
27. Vanchinathan, S., Ph.D. Thesis. Modeling and control of kraft pulping based on cooking liquor analysis, Auburn University, 1995. Tappi J., 1996, 79(10):187–191
28. U.S. Pat. No. 5,616,214. Leclerc
29. Phelan et al. Anal. Chem., 1989, 61(3), 1419–24
30. WO98/10137—Fisher Rosemont Systems, Inc.; Mar. 12, 1998.

SUMMARY OF THE INVENTION

It is an object of the present invention to provide a rapid method for determining the concentration of $OH^-$, $CO_3^=$ and $HS^-$ species in aqueous solution, particularly in solutions containing all three species.

It is a further object to provide a rapid method for determining the concentration of organic species present in a pulping process liquor, particularly, in the presence of at least one of the species selected from $OH^-$, $CO_3^=$ and $HS^-$.

It is a further object to provide a rapid method for determining the concentration of effective alkali, residual alkali, sodium sulfide, sodium carbonate and dead-load components such as chloride and dissolved organic species in pulp liquors.

It is a further object of the present invention to provide a rapid method for determining the concentrations of sulphate and thiosulphate in the presence of $OH^-$, $CO_3^{2-}$, or $HS^-$, particularly in solutions containing two or more of these species.

It is a further object of the present invention to provide a rapid method for determining the concentrations of polysulphide in the presence of $OH^-$, $CO_3^{2-}$, and $HS^-$, particularly in solutions containing all four species.

It is a further object to provide a rapid method for determining the concentration of peroxide ions in the presence of $OH^-$, $CO_3^{2-}$, and $HS^-$, particularly in the presence of two or more of these species.

It is a further object to provide an improved method for the analysis of chlorate and sulfuric acid.

It is a yet further object to provide said rapid process which does not need frequent equipment maintenance, sample pretreatment or chemical reagents.

It is a still yet further object to provide said method which, optionally, allows a plurality of pulp liquor process streams to be multiplexed to a single analyser in a fibre-optic network.

It is a further object to provide apparatus for effecting said methods.

Accordingly, the invention provides in one aspect a method for determining the concentration of hydrogen ion, organic anionic species and anionic species selected from the group consisting of $OH^-$, $CO_3^=$, $HS^-$, $ClO_3^-$, $SO_4^=$, $S_2O_3^=$, polysulphide and peroxide in an aqueous sample solution, said method comprising subjecting said solution to near infrared radiation at a wavelength region of wave numbers selected from about 7,000 to 14,000 cm$^{-1}$ through a solution path length of at least 3 mm to obtain spectral data for said solution; obtaining comparative spectral data for said anionic species at known concentrations in aqueous solutions; and correlating by multivariate calibration the relationships between said spectral data of said sample solution and said comparative spectral data to determine said concentration of said anionic species in said sample solution.

Preferably, the wavelength is selected from 7,000 to 12,000 cm$^{-1}$, and more preferably, 9,000 to 12,000 cm$^{-1}$.

The spectral data is preferably obtained by transmittance spectrophotometry, and more preferably, from a transmission cell. The relationships between the spectral data of the sample and the comparative spectral data are, preferably, obtained with a partial-least-squares multivariate calibration.

In a preferred aspect the invention provides a process for controlling the operation of individual unit operations within a cellulosic pulp manufacturing process, which comprises the steps of:

subjecting samples of process liquors to near infrared radiation at a wavelength region of wavenumbers from about 7,000 to 14,000 cm$^{-1}$ to produce measurements of said liquor;

recording the spectrum of different mixture solutions of synthetic and process liquors having known concentration parameters;

correlating by multivariate calibration the relationships between the spectra of the process liquor samples and the different mixture solutions of known concentration parameters so as to simultaneously determine concentration parameters in the process liquor samples; and adjusting the individual unit operations of the cellulosic pulp manufacturing process as required by controlling at least one process parameter to bring the final product of said unit operation to a desired value, wherein said final product is determined in part by concentration parameters in said process liquors, as determined by the near infrared measurements of said concentration parameters.

Thus, the invention, in a preferred aspect, provides a rapid method for the control of a cellulosic pulp manufacturing process via on-line measurement of chemical concentration parameters in process liquor streams with near infrared radiation. The method eliminates the need for (i) manual sampling, (ii) frequent equipment maintenance, (iii) a dedicated instrument at each sampling point, (iv) compensation for instrumental drift, and, optionally, (v) an environmentally controlled spectrometer housing near the sampling location(s). The method includes the steps of (i) withdrawing samples of a process liquor stream from a cellulosic pulp manufacturing process, (ii) subjecting the samples to near-infrared spectrophotometry over a predetermined range of wavenumbers so as to produce spectral measurements which determine the concentrations of different combinations of chemical components, (iii) correlating by multivariate calibration the relationships between the spectral measurements of unknown samples and the spectral variations shown by different combinations of chemical components of the process liquor so that concentration parameters can be accurately determined for typical levels of chemical components present in the process liquor, and (iv) controlling at least one process parameter so as to obtain optimal operation of the cellulosic pulp manufacturing process.

The method of the present invention uses "wide-bore" near infrared spectrometry, i.e. wherein the cell path of the solution subjected to the near infrared radiation is at least 3 mm, preferably 3–20 mm, and more preferably 5–12 mm. This clearly distinguishes the invention over prior art methods (27, 28) which teach the use of "narrow-bore" path lengths of <2 mm, when measuring the first overtone of the near infrared (approximately 4,000–7,000 cm$^{-1}$), or <1×10$^{-3}$ cm when measuring the mid-infrared region (approximately 4,000–400 cm$^{-1}$).

The present invention is thus of significant value in providing for the rapid determination of the alkalinity OH$^-$, $CO_3^=$ and HS$^-$ levels in pulp liquors, which contains inter alia, all three species in varying amounts, and also for $ClO_3^-$, $SO_4^=$, $S_2O_3^=$, polysulfide, and peroxide anions.

Surprisingly, the invention provides that although signal strengths of the water absorption bonds diminish with increasing wavenumber from the infrared to the visible spectral range, increasing the sample path length enables sufficient signal absorption to occur in multi anionic species-containing solutions, within the background noise to enable enhanced accurate spectral data on each of the anionic species to be obtained. Such rapid and accurate anionic species concentration of the order of ±1 g/L in pulp liquors allows for good and beneficial control of pulp liquor concentrations.

Cellulosic pulp cooking liquor which has been extracted from the cooking process at some point after coming into contact with the wood chips is collectively referred to as black liquor. The actual composition of any black liquor can vary substantially with a strong dependence on the time and location of extraction, the original composition of the wood and/or liquor upon entering the digester, and the cooking conditions. The dissolved substances in black liquor fall into two primary categories: total inorganic content and total organic content. The inorganic content, which constitutes 25 to 40% of the dissolved substances, consists primarily of anionic species such as hydroxide, hydrosulfide, carbonate, chloride, sulfate, sulfite and thiosulfate, where sodium is the primary counter ion. The organic content, which constitutes the remaining 60 to 75% of the dissolved substances, can be further divided into three main categories: lignin—aromatic organic compounds (30–45%), carbohydrates—hemicelluloses and cellulose degradation products (28–36%), and extractives—fatty and resinous acids (3–5%). These organic species provide unique contributions to the overall electromagnetic spectral signature of a black liquor sample. Therefore, it is possible to relate the near infrared spectrum of a black liquor sample to the total or constituent organic content of that liquor for calibration purposes. In this way, it is possible to simultaneously measure, for example, the lignin and the sodium hydroxide (or EA) content of a black liquor extracted from a digester. In a more general sense, the total organic content and the total inorganic content, as well as the sum of these two constituents (i.e., the total dissolved solids) would also be quantifiable in a similar manner. Surprisingly, the transmission of near infrared radiation through black liquor is still great enough to quantify these components even when a pathlength of 10 mm is used.

Thus, the present invention provides a rapid method for determining effective alkali, residual effective alkali, sodium sulfide, sodium carbonate, and dead-load components, such as sodium chloride, sodium sulfite, sodium sulfate, sodium thiosulfate and dissolved organic species in process liquors and controlling appropriate parameters in the cellulosic pulp manufacturing process based on the determined values. The proposed method largely eliminates the need for frequent equipment maintenance, sample pretreatment and the use of chemical reagents. High sample throughput can also be obtained by allowing many process streams to be multiplexed to a single analyser through an optional fiber-optic network.

Samples of process liquors are analysed by near-infrared Fourier transform infrared (FT-IR) spectrometry. Spectra are collected using a flow-through wide-bore transmittance accessory. The absorbance of the liquor is measured over a predetermined wavelength region. The absorbance is then correlated through a multivariate regression method known in the art as partial least-squares (PLS) with the concentration of the absorbing compound. This correlation is made by comparing results previously obtained with standard samples. The chemical composition of the liquor is then calculated. The process samples are also analysed with either standard CPPA, SCAN or TAPPI analytical methods, to establish a correlation with the data obtained by near-infrared spectrometry.

The on-line method for EA and REA may primarily be used for controlling the operation of either batch or continuous digesters. The blow-line kappa number can then be predicted by using its well-known relationship with the REA. The method can also be used for controlling carbonate and hydroxide levels in green and white liquors. The causticizing efficiency could also be calculated. In summary, this new sensing and control method could replace automatic titrators and conductivity sensors. It would also give previously unavailable information on the carbonate levels in process liquors, while improving the control of scaling in multi-effect evaporators.

In a preferred aspect, the present invention provides a method for measuring effective alkali in a kraft pulp manufacturing process and controlling the appropriate process parameters said method comprising the steps of:
  subjecting samples of process liquors to near infrared radiation at a wavelength region of wavenumbers from about 7,000 to 14,000 $cm^{-1}$ to produce measurements of said liquor;
  recording the spectrum of different mixture solutions of synthetic and process liquors having known EA;
  correlating by multivariate calibration the relationships between the spectra of the process liquor samples and the different mixture solutions of known EA so as to simultaneously determine EA in the process liquor samples; and
  adjusting the cooking conditions selected from time and temperature of the kraft pulp manufacturing process by controlling at least one process parameter to bring said cooking conditions as determined by said near infrared measurements on the process liquor to desired values.

In a further aspect the invention also provides an apparatus for determining the concentration of hydrogen ion and an anionic species selected from the group consisting of $OH^-$, $CO_3^=$, $ClO_3^-$, $SO_4^=$, $S_2O_3^=$, polysulfide, peroxide and $HS^-$ in an aqueous solution, said apparatus comprising sample means for providing said sample with a solution path length of not less than 3 mm; Fourier transform near infrared means for subjecting said solution over said path length to near infrared radiation at a wavelength region of wavenumbers selected from about 7,000 to 14,000 $cm^{-1}$; and spectral recordal means for recording spectral data of said radiation after subjecting said solution to said radiation.

BRIEF DESCRIPTION OF THE DRAWINGS

In order that the invention may be better understood, preferred embodiments will now be described by way of example, only, wherein.

DESCRIPTION OF PREFERRED EMBODIMENTS

Figure 1A:
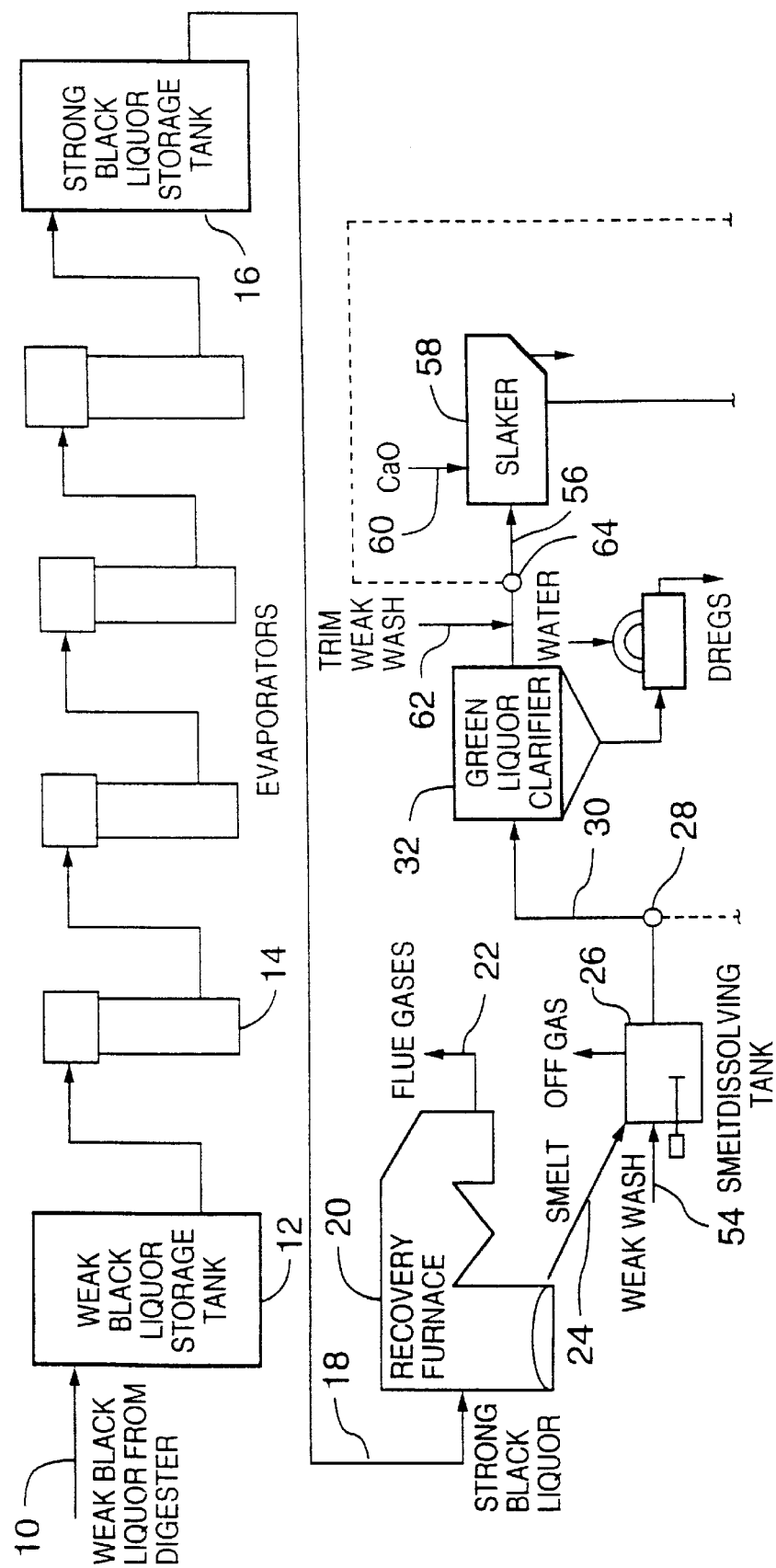
FIG. 1 is a diagrammatic view of the recovery and recausticizing process system, complete with sensing and control apparatus according to one embodiment of the present invention.
Figure 1B:
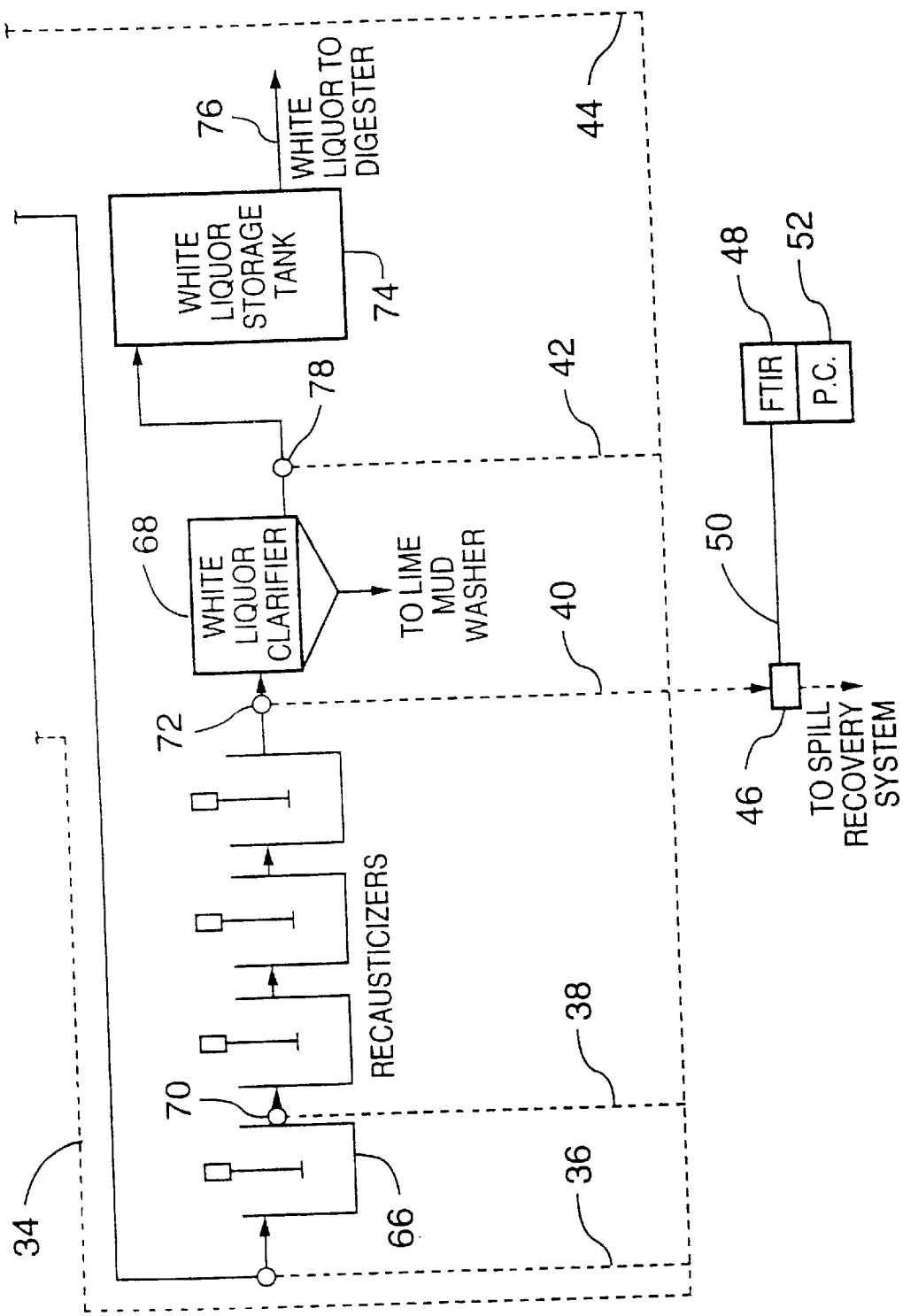
Figure 12:
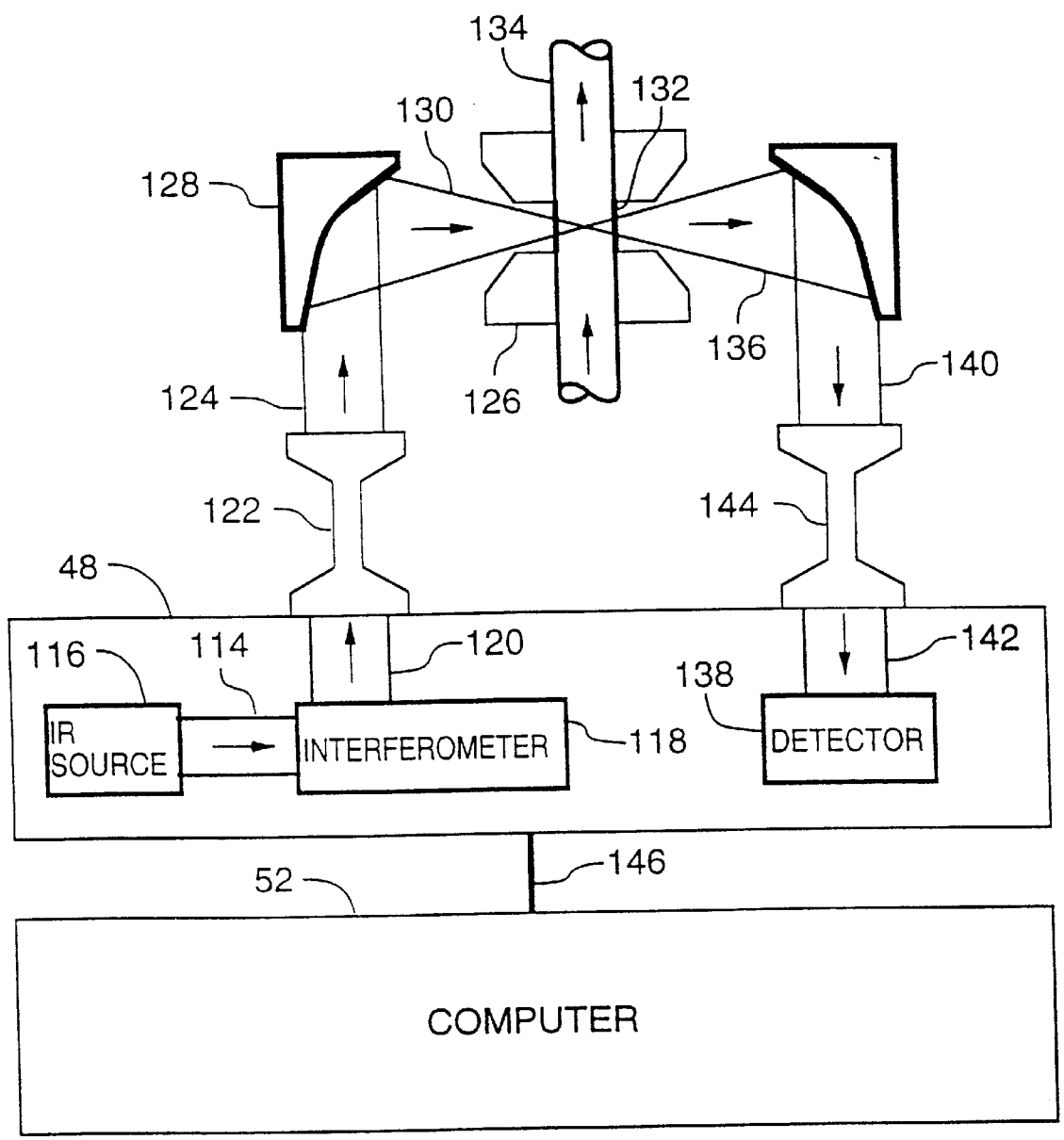
FIG. 12 is a diagrammatic view of sensing apparatus of use in the practice of the present invention.

FIG. 1 is a diagrammatic view of a recovery system, complete with sensing apparatus, according to one embodiment of the present invention. The sensing apparatus shown in FIG. 12 is further described, hereinafter.

Referring to FIG. 1, weak black liquor recovered from the digestion process may be temporarily stored in a weak black liquor storage tank 12 before being concentrated through multiple-effect evaporators 14 to form strong black liquor which is stored in a strong black liquor storage tank 16. Line 18 delivers the strong black liquor from the strong black liquor storage tank 16 to the recovery furnace 20 to generate flue gases 22 and smelt 24. The smelt 24 flows to the smelt dissolving tank 26 to form green liquor. Green liquor samples are taken at sample withdrawal point 28 in line 30 leading to the green liquor clarifier 32. The samples are fed through a 1.25 cm diameter conduit 34, optionally merged with other optional sample streams 36, 38, 40, 42 and/or 44, through either a transmittance-mode or a reflectance-mode flow-cell 46, well-known in the art. Infrared light from an infrared source which is integral to a Fourier transform spectrometer 48 is brought to the flow-cell 46 by means of a direct optical coupling with mirrors or by a fiber optic cable 50. Some of the infrared light is absorbed by the liquor and the residual light is returned to the Fourier transform spectrometer by means of either a direct optical coupling with mirrors or by a second fiber optic cable 50. The spectrometer 48 records the near-infrared single-beam spectrum of the liquor. Readings from the spectrometer 48 are transferred to a computer 52 which calculates the individual component concentrations of the liquor, such as, sodium hydroxide, sodium sulfide, sodium carbonate, and optionally, sodium chloride with the use of a PLS multi-component calibration model. The concentration parameters of conversion efficiency and/or causticity and/or total titratable alkali (TTA) are calculated from said concentrations automatically by the computer 52.

The concentration parameter of TTA is used to automatically control the flow of weak wash 54 entering the smelt dissolving tank so as to obtain an optimal value of TTA in the unclarified green liquor leaving the smelt dissolving tank 26 through flow line 30 which transports said liquor to the green liquor clarifier 32.

Liquor in line 56 flows from the green liquor clarifier 32 and enters the slaker 50 where a variable quantity of calcium oxide is added through line 60 to form calcium hydroxide. Trim weak wash 62 is added to line 56 immediately before sample withdrawal point 64 which transfers a sample through line 44 to the flow cell 46 for analysis. The concentration parameter TTA is calculated by the computer 52 and used as feedback control of the trim weak wash line 62 flow rate, and/or feedforward control of the calcium oxide line feed rate 60 to the slaker 58.

Upon leaving the slaker, the liquor flows through a series of three or more recausticizers 66 which allow most of the sodium carbonate to react with the calcium hydroxide to form sodium hydroxide and calcium carbonate. The resulting suspension then proceeds to the white liquor clarifier 68. The partially recausticized white liquor is sampled from withdrawal point 70 and/or 72 where it is delivered to the flow cell 48 where the concentrations of sodium hydroxide, sodium sulfide, sodium carbonate, and optionally, sodium chloride, are simultaneously determined. The concentration parameter of causticity is calculated from these values and used as fast feedback control of the feed rate of calcium oxide to the slaker through line 60 if withdrawal point 70 is used or slow feedback control of said feed rate if withdrawal point 72 is used. The clarified white liquor leaves the white liquor clarifier 68 and flows to the white liquor storage tank 74 where it is ready for use in the digestion process through line 76. If the retention time of the white liquor clarifier 68 is sufficiently short, as in the case of pressure or disk filters used for clarifying, withdrawal point 78 may be used in place of withdrawal point 72.

Figure 2:
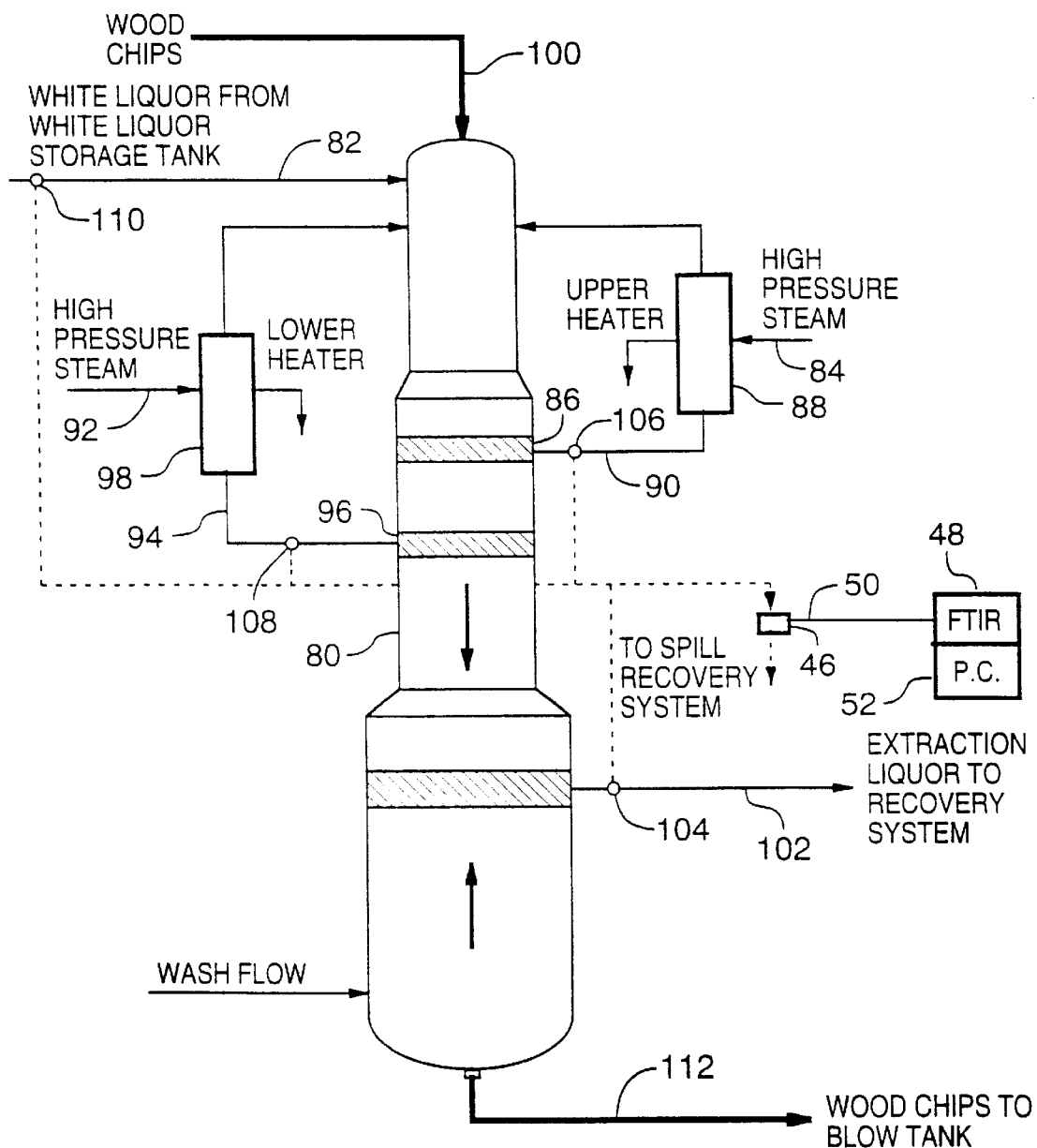
FIG. 2 is a diagrammatic view of a pulp digester, complete with sensing and control apparatus according to a further embodiment of the present invention.
Figure 3:
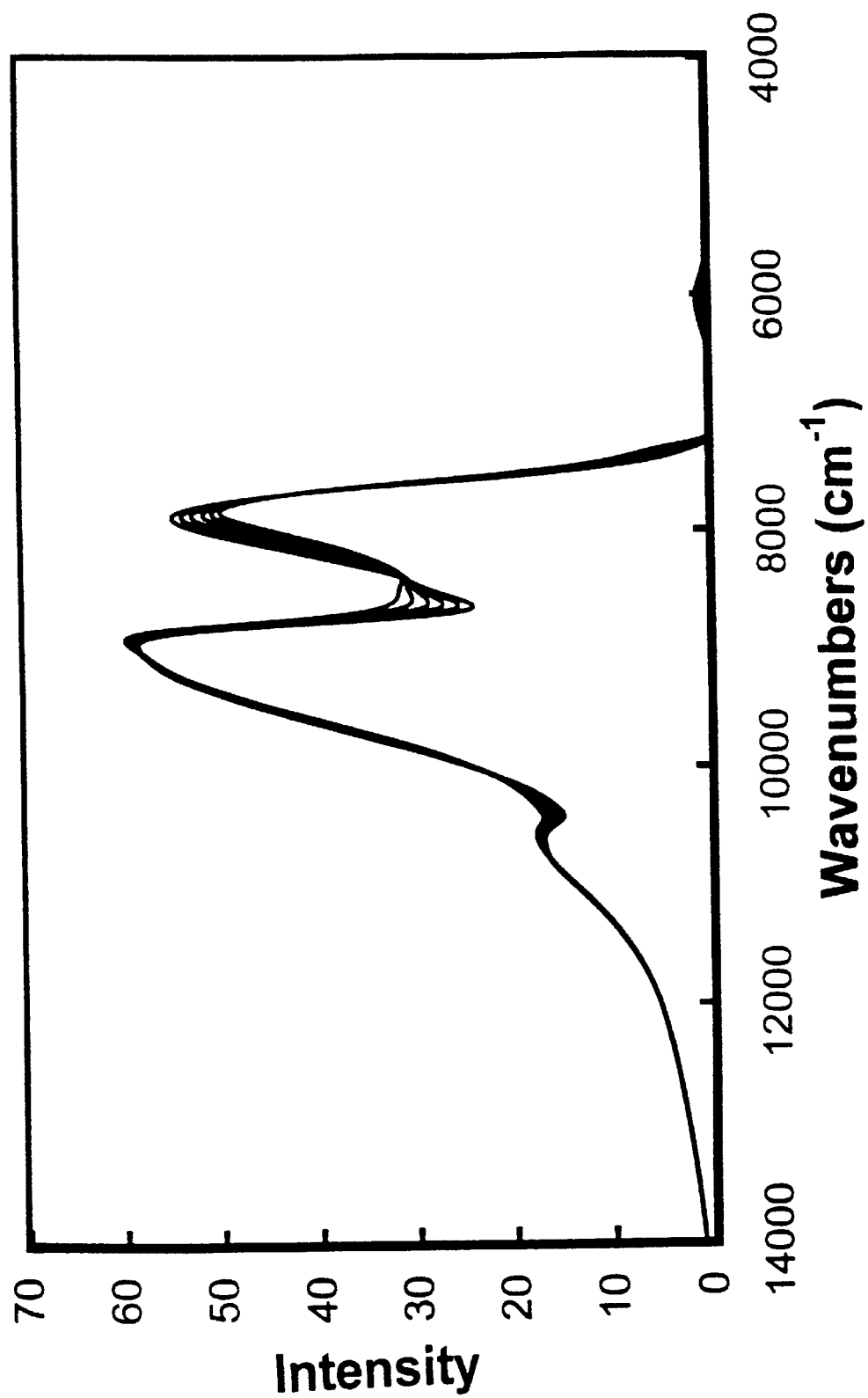
FIG. 3 is a graph of absorbance versus reciprocal centimeters showing the change in near-infrared absorbance with respect to an air reference between 4000 and 14000 wavenumbers for a range of temperatures selected from between 5 and 25° C.

FIG. 2, shows a diagrammatic representation of a continuous type Kamyr digester and of a control system as embodied by the invention. This control system may be used to monitor the effective alkali (EA) consumption during the impregnation and cooking stages of a continuous cooking pulping operation. EA is a concentration parameter defined as the sodium hydroxide plus half of the sodium sulfide (expressed as $Na_2O$) present in a mill liquor. Referring to FIG. 2, a digester 80 is shown with a white liquor supply line 82 from the white liquor storage tank (not shown). The liquor in the digester 80 is indirectly heated through a transfer line by high pressure steam supplied through a steam supply line 84. Black liquor is withdrawn from the digester 80 through the upper circulation screen 86 and then sent through an upper heater 88 using a recirculating loop 90. A second steam line 92 provides steam to a second recirculation loop 94 in which the liquor is withdrawn from the digester 80 through the lower circulation screen 96 and sent to a lower heater 98.

Chips are fed to the digester 80 through line 100. Samples from the digester are withdrawn from the extraction liquor line 102 at withdrawal point 104. For other tests, samples are withdrawn from the sample point 106 in the upper heater loop, sample point 108 in the lower heater loop, and sample point 110 in the white liquor supply line 82. The samples are fed individually through 1.25 cm conduits by a means of valves, and merged with each other before flowing through either a transmittance-mode or a reflectance-mode flow-cell 46, for which either mode is well-known in the art. Infrared light from an infrared source which is integral to a Fourier transform spectrometer 48 is brought to the flow-cell 46 by means of a direct optical coupling with mirrors or by a fiber optic cable 50. Some of the infrared light is absorbed by the liquor and the residual light is returned to the Fourier transform spectrometer by means of either a direct optical coupling with mirrors or by a second fiber optic cable 50. The spectrometer 48 records the near-infrared single-beam spectrum of the liquor. Readings from the spectrometer 48 are transferred to a computer 52 which determines the EA and sulfidity of the white liquor, and the EA and total organic content of the black liquor with the use of a PLS multicomponent calibration model. The white liquor EA is used to control the ratio of EA to wood in the digester by adjusting the feed rate of white liquor. Black liquor EA is used to ensure that the residual EA present in the cook zones is sufficient to ensure dissolution of the lignin present in wood chips while not exceeding a lower set-point and is achieved by adjusting the EA to wood ratio. White liquor sulfidity, black liquor EA and total organic content are used as a feedforward signal for kappa or k-number control by adjustment of the cooking conditions, such as temperature and time, of the digester. This can be done by adjusting the production rate and the temperature of the upper and/or lower circulation heaters 88 and 98, respectively. The extraction liquor flows through line 102 to the flash tanks (not shown) on its way to the recovery cycle. Digested wood chips exit through the blow line 112 to the blow tank (not shown) before entering the brownstock washing stage.

FIG. 12 shows the interface between the liquor sample and the Fourier transform spectrophotometer (e.g., Bomem, Hartmann and Braun, WorkIR 160) in greater detail. A beam of infrared light 114 leaves the infrared source 116 within the Fourier transform spectrometer, 48 and enters an interferometer 118. Light 120 leaving the interferometer 118 enters an optional fiber-optic extension accessory 122 which includes (i) an entrance lens which concentrates the wide incoming beam (perhaps 30 mm) down onto the 0.6 mm diameter fiber, (ii) a variable length of fiber-optic cable (as much as 300 m or more), and (iii) an exit lens which expands the narrow beam of the fiber back to a wide beam of similar width to the incoming beam. The spectrometer may also be coupled directly to the transmission cell over relatively short distances by eliminating the fiber-optic extension accessory. The beam of infrared light 124 leaving the exit lens of the fiber-optic extension accessory is focussed through the 316 stainless steel transmission cell 126 by parabolic mirror 128. The beam 130 passes through two caustic-resistant windows 132 (e.g. Harrick Scientific, BK-7) which contain the flowing or static liquor in the transmission cell 126. The liquor arrives in and leaves from the transmission cell via 316 stainless steel sample conduit 134. The infrared beam 136 is then redirected back into the spectrometer and onto the germanium (Ge) detector 138 via route 140 and 142 with the option of extending this distance with the fiber-optic extension accessory 144 in a similar way that the beam 120 leaving the interferometer 118 was extended. After a complete scan of the wavelength region of interest, the spectrometer transfers the resulting interferogram to an acquisition card located in an IBM-compatible personal computer 52 via serial cable 146. The spectrum can then be computed by the acquisition card and several spectra (e.g. 128) can be co-added by the computer software. The resulting averaged spectrum can then be used to calculate the individual component concentrations of the liquor such as sodium hydroxide, sodium sulfide, sodium carbonate, and optionally, sodium chloride with the use of a PLS multicomponent calibration model. The concentration parameters of conversion efficiency and/or causticity and/or total titratable alkali (TTA) are calculated from said concentrations automatically by the computer.

EXAMPLE 1

Figure 4:
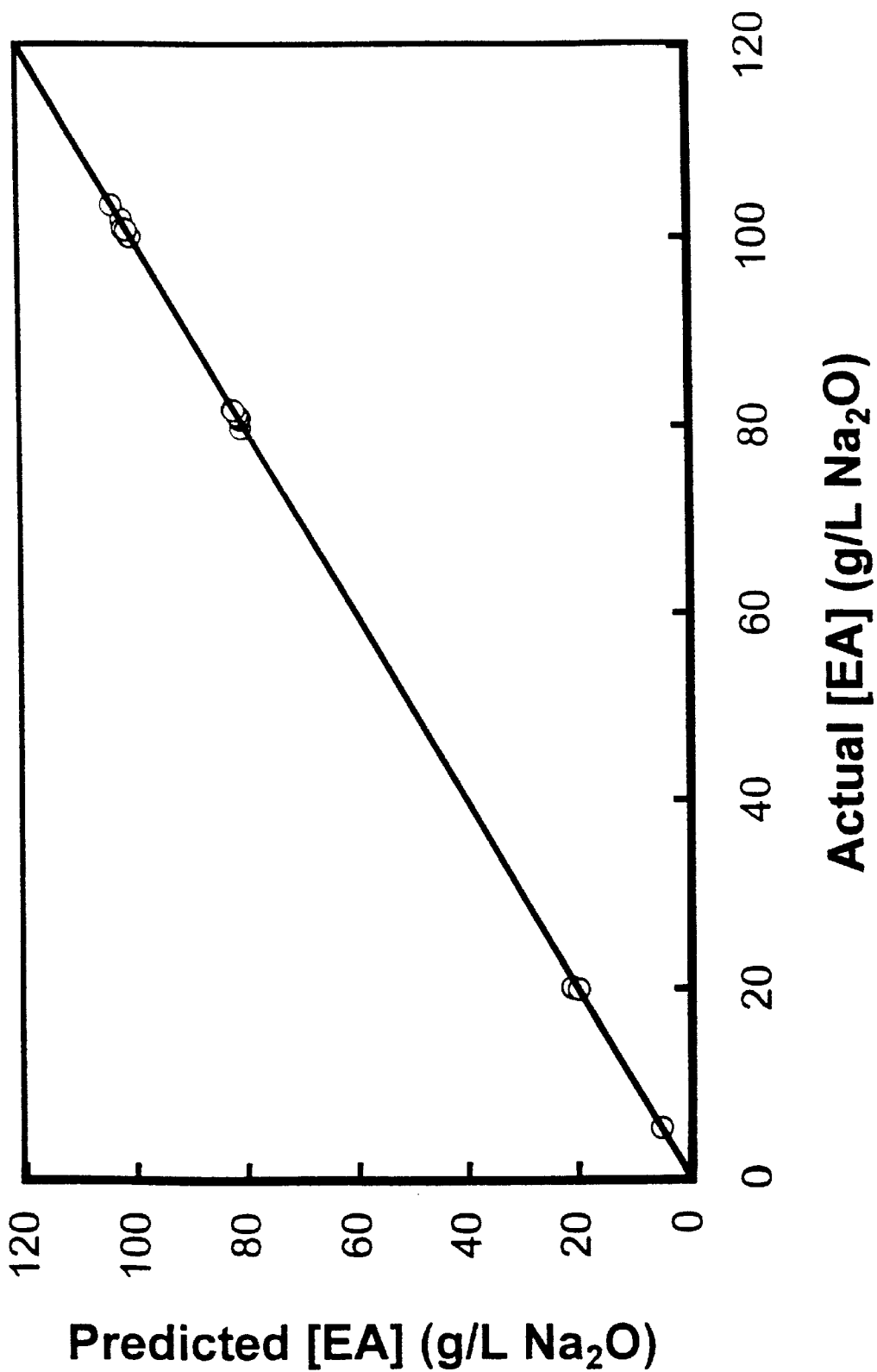
FIG. 4 is a PLS calibration graph of the predicted versus actual EA concentration for the three-component PLS calibration model.
Figure 5:
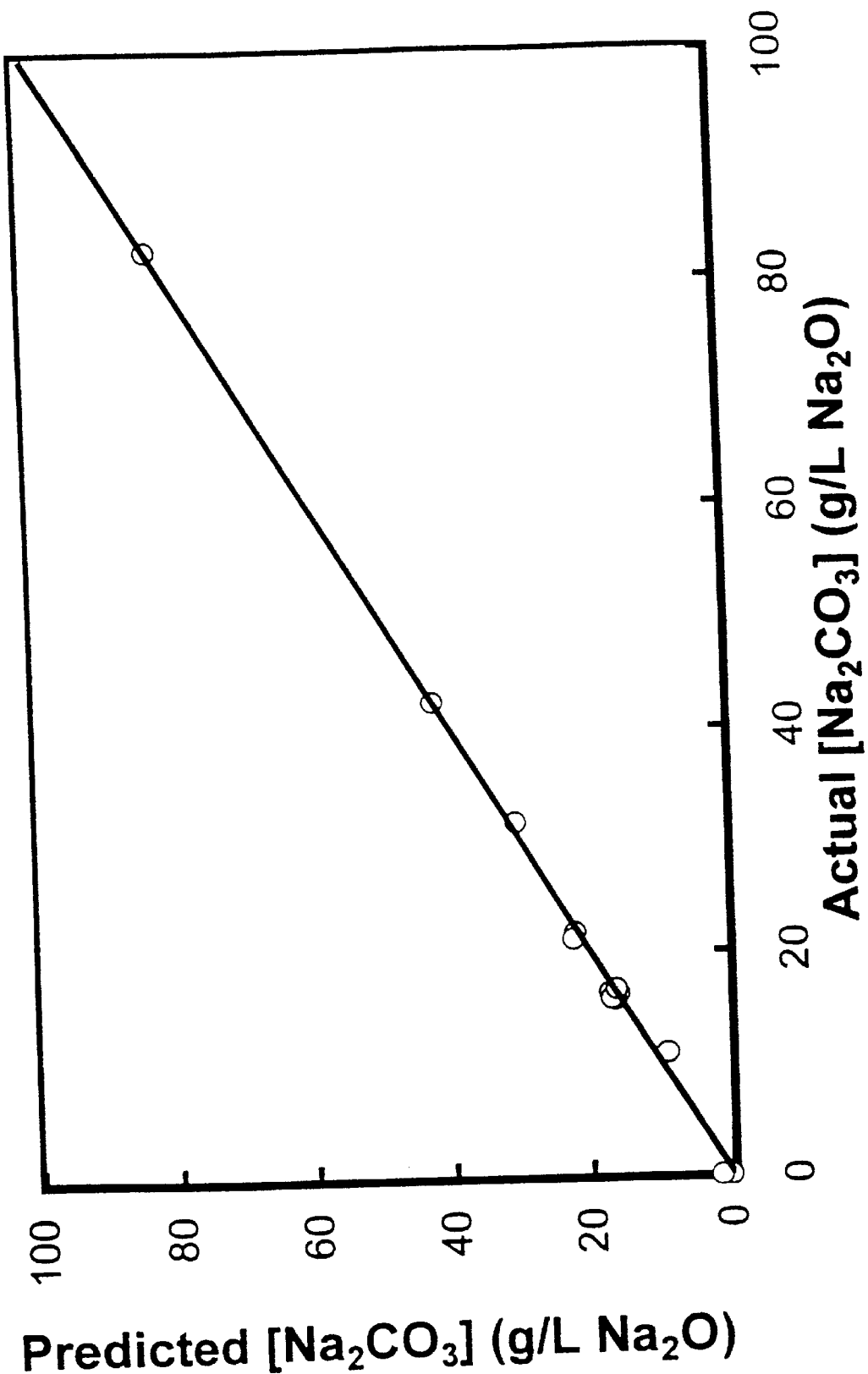
FIG. 5 is a PLS calibration graph of the predicted versus actual sodium carbonate concentration for the three-component PLS calibration model.
Figure 6:
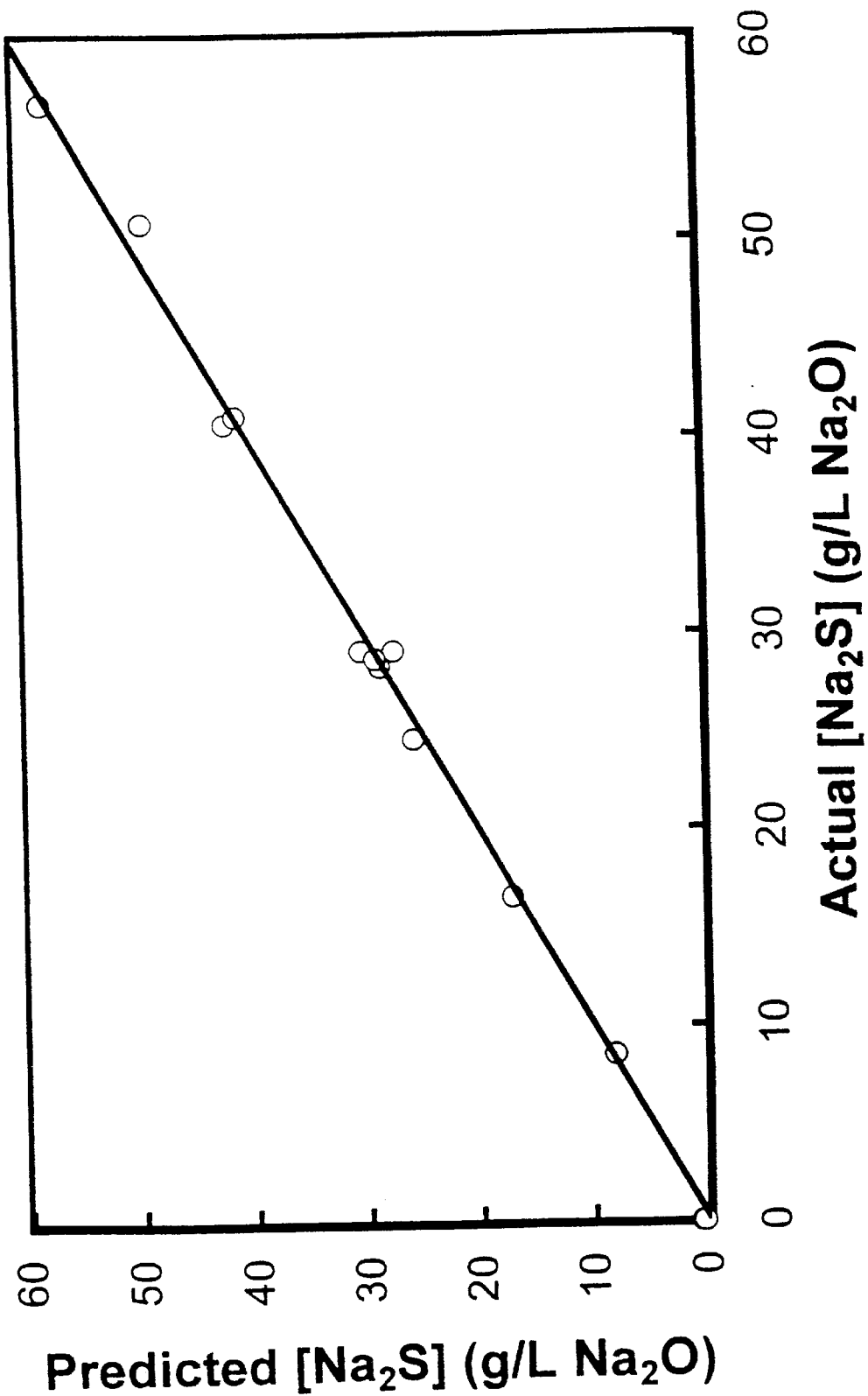
FIG. 6 is a PLS calibration graph of the predicted versus actual hydrosulfide concentration for the three-component PLS calibration model.

A three-component PLS calibration was performed on the set of synthetic samples listed in Table I for the purpose of building a calibration model that is capable of predicting 1) effective alkali concentrations 2) sodium sulfide concentrations and 3) sodium carbonate concentrations. The spectral region chosen for building the model was from 11000 to 7300 wavenumbers ($cm^{-1}$) for all three components. The calibration graphs are shown in FIG. 4 (effective alkali), FIG. 5 (carbonate) and FIG. 6 (sulfidity), all of which demonstrate good agreement between predicted and actual values. The standard deviation of the differences between the actual and predicted values are (all in g/L as $Na_2O$) 0.34 for effective alkali, 1.0 for sulfidity, and 1.1 for carbonate. From the predicted concentrations shown herein, it is possible to calculate TTA, % sulfidity, and causticity for purposes of control.

TABLE I

Compositions of synthetic liquor samples used for the three-component PLS Calibration

| Sample No. | Effective Alkali (g/L as $Na_2O$) | Sodium Sulfide (g/L as $Na_2O$) | Sodium Carbonate (g/L as $Na_2O$) |
| --- | --- | --- | --- |
| 1  | 100.2 | 0    | 0    |
| 2  | 5.2   | 0    | 0    |
| 3  | 102.0 | 24.6 | 0    |
| 4  | 103.5 | 56.8 | 0    |
| 5  | 101.0 | 0    | 42.5 |
| 6  | 100.2 | 0    | 82.8 |
| 7  | 100.9 | 50.9 | 21.8 |
| 8  | 20.2  | 40.7 | 0    |
| 9  | 79.9  | 28.3 | 11.0 |
| 10 | 81.0  | 29.1 | 21.2 |
| 11 | 81.9  | 29.1 | 31.6 |
| 12 | 81.0  | 8.5  | 16.4 |
| 13 | 80.8  | 16.6 | 16.3 |
| 14 | 81.1  | 28.7 | 15.8 |
| 15 | 81.3  | 41.1 | 15.9 |
| 16 | 20.0  | 0    | 0    |
| 17 | 81.8  | 0    | 16.7 |

EXAMPLE 2

Figure 7:
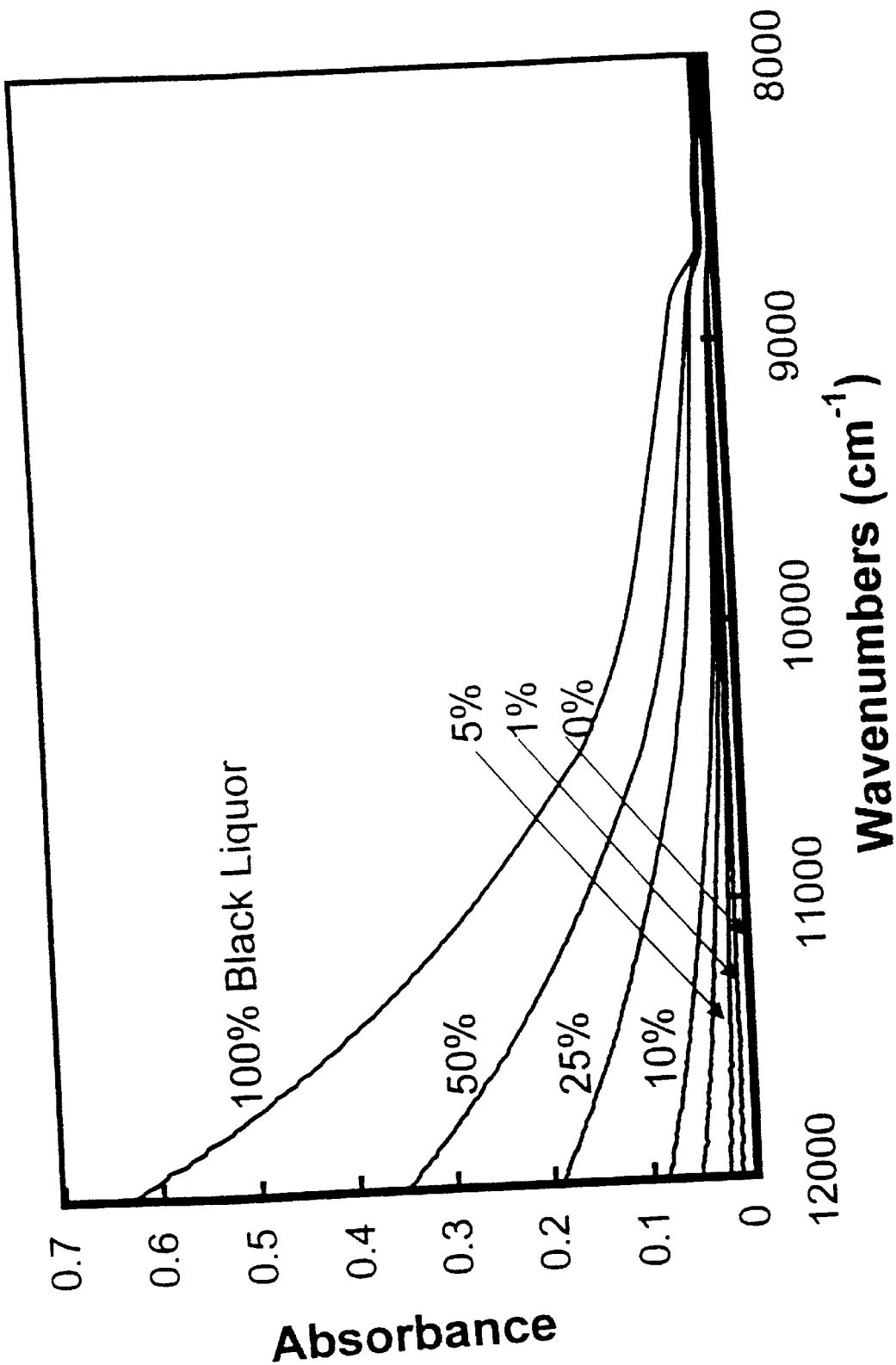
FIG. 7 is a graph of absorbance versus reciprocal centimetres showing the change in near-infrared absorbance for a range of diluted black liquors with respect to a 10 g/L EA reference between 4000 and 14000 wave numbers.
Figure 8:
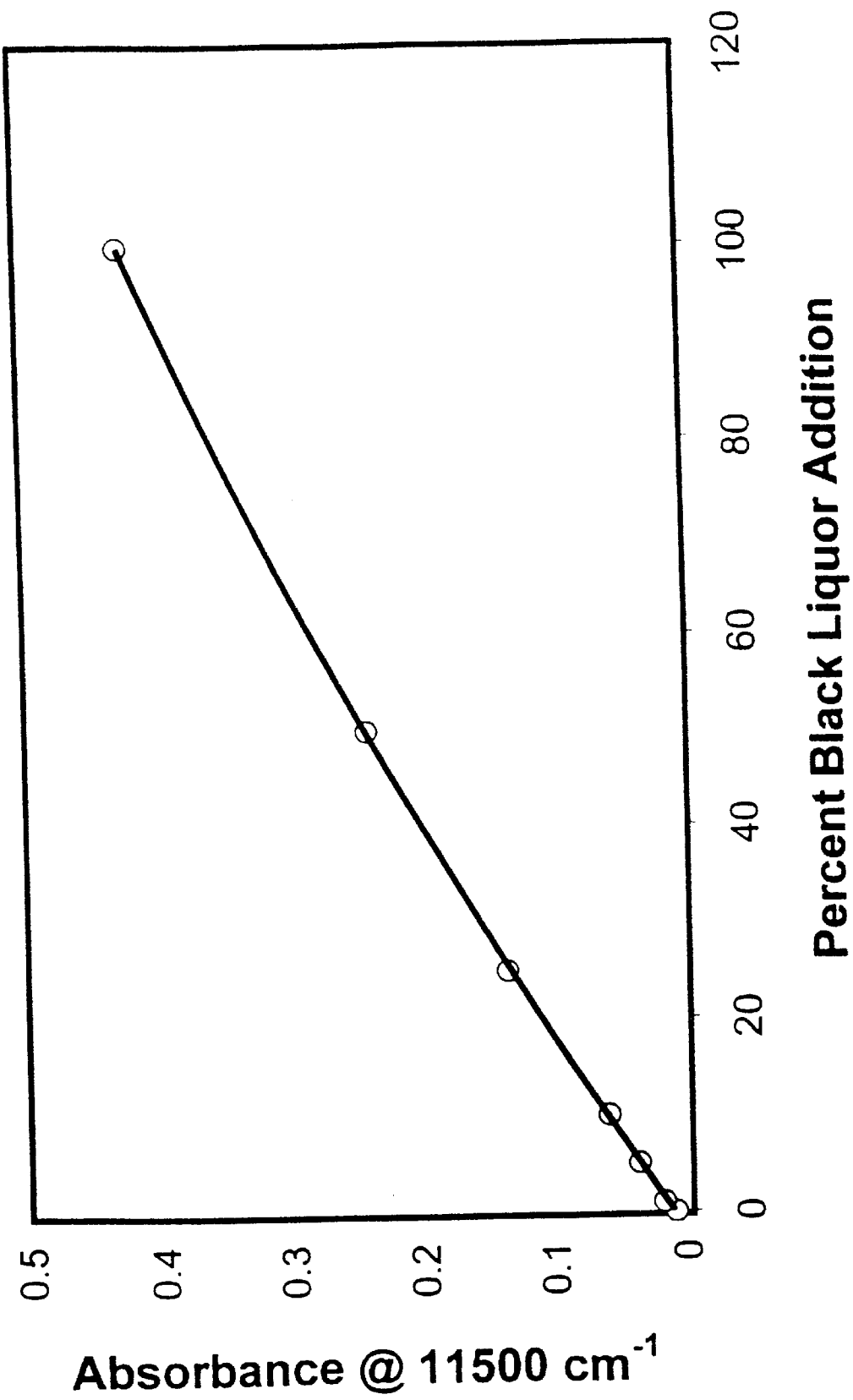
FIG. 8 is a graph of absorbance versus percent black liquor added showing the change in near-infrared absorbance at 11500 $cm^{-1}$ for a range of diluted black liquors with respect to a 10 g/L EA reference.

The absorbance spectra of samples consisting of various dilutions of a black liquor sample are shown in FIG. 7. There is clearly a strong correlation between the dilution of the black liquor and the absorbance in the region between wavenumbers 12000 to 9000 ($cm^{-1}$). A calibration graph is shown in FIG. 8 based on the absorbance at 11500 wavenumbers ($cm^{-1}$). The trend is slightly non-linear, and a good fit is shown by the second order polynomial trendline.

EXAMPLE 3

Figure 9:
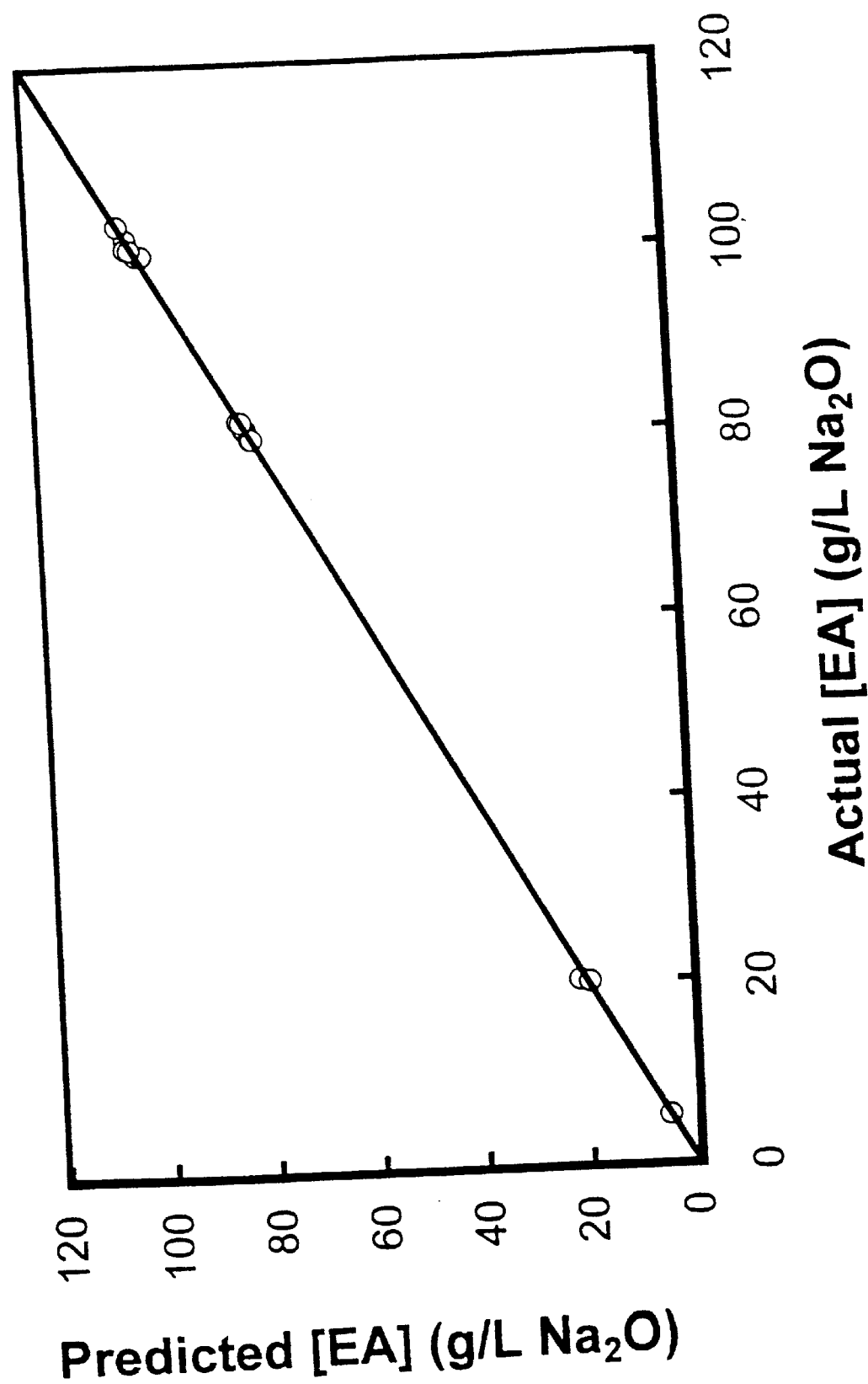
FIG. 9 is a PLS calibration graph of the predicted versus actual EA concentration for the three-component PLS calibration model with sodium chloride added as an interference.
Figure 10:
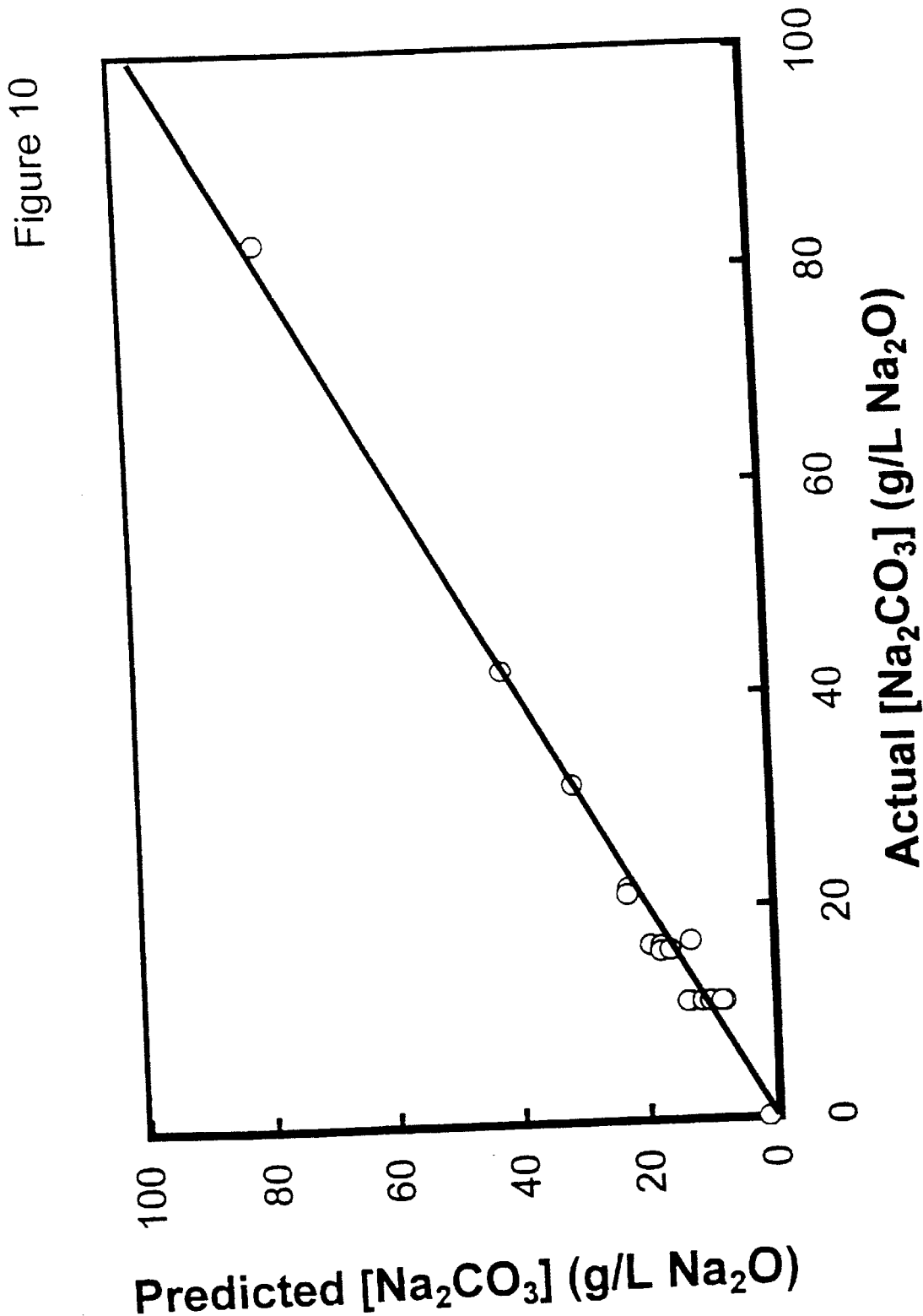
FIG. 10 is a PLS calibration graph of the predicted versus actual sodium carbonate concentration for the three-component PLS calibration model with sodium chloride added as an interference.
Figure 11:
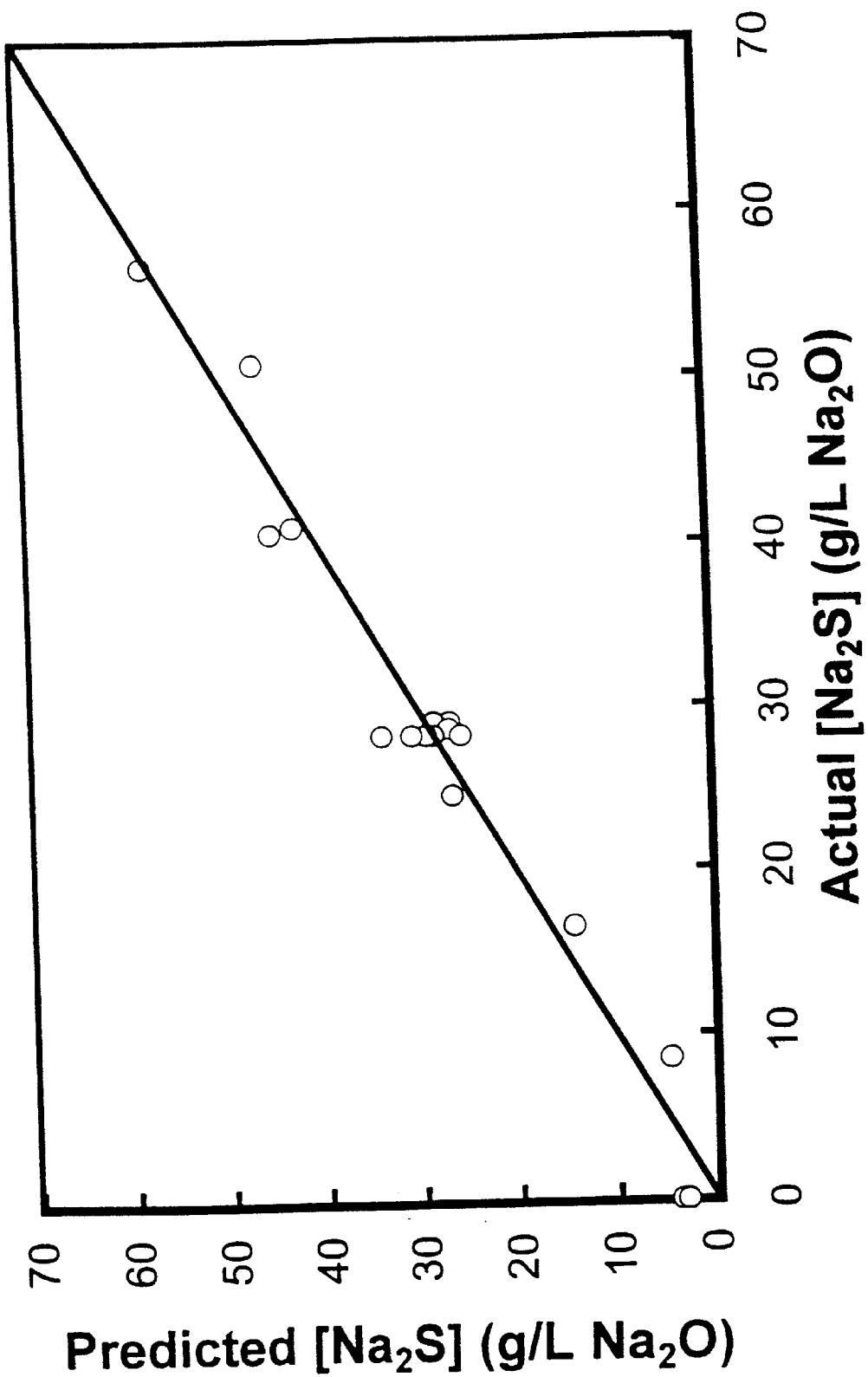
FIG. 11 is a PLS calibration graph of the predicted versus actual sodium sulfide concentration for the three-component PLS calibration model with sodium chloride added as an interference.

The accuracy of the PLS model calibrated for EA, sodium sulfide, and sodium carbonate concentrations was investigated to see how it was affected by varying sodium chloride concentrations from 0 to 40 g/L (as NaCl). Synthetic solutions were made up of fixed concentrations of EA, sodium sulfide, sodium carbonate, and varying concentrations of sodium chloride. The concentrations of all the components except sodium chloride were included in the model, which was generated from the samples in Table I (all of which contained no sodium chloride) and Table II (concentrations as shown). The model still accurately predicts EA (shown in FIG. 9), sodium carbonate (shown in FIG. 10), and sodium sulfide (shown in FIG. 11) for solutions regardless of sodium chloride concentration.

TABLE II

Compositions of synthetic liquor samples added to three-component PLS Calibration

| Sample No. | Effective Alkali (g/L as Na$_2$O) | Sodium Sulfide (g/L as Na$_2$O) | Sodium Carbonate (g/L as Na$_2$O) | Sodium Chloride (g/L as NaCl) |
|---|---|---|---|---|
| 18 | 79.9 | 28.3 | 11.0 | 0 |
| 19 | 79.9 | 28.3 | 11.0 | 10 |
| 20 | 79.9 | 28.3 | 11.0 | 20 |
| 21 | 79.9 | 28.3 | 11.0 | 30 |
| 22 | 79.9 | 28.3 | 11.0 | 40 |

From the above examples it can be seen that different types of process liquors in the cellulosic pulp manufacturing process can be analyzed and that concentration parameters can be simultaneously determined with the use of various types of partial least squares (PLS) multivariate calibration which correlate the spectral behavior for different concentrations of each chemical component in a calibration sample with their actual concentration in that sample. The set of correlations represents a model which can then be used to predict the concentration parameters of an unknown sample. Consequently, by varying at least one process variable, the process can be controlled so that optimal production of desired product is obtained.

EXAMPLE 4

Figure 13:
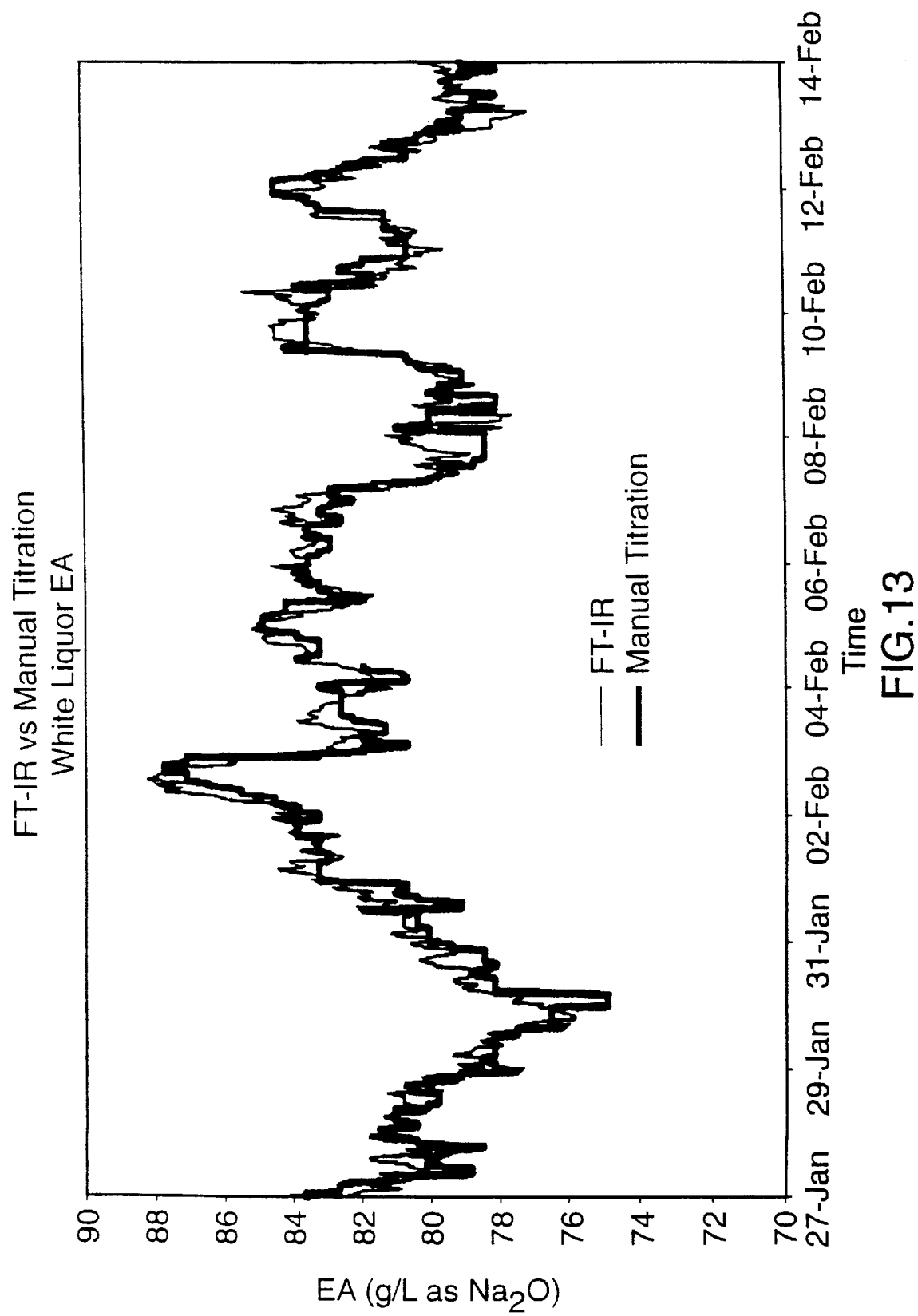
FIG. 13 is a plot of the concentration of white liquor being fed into the B digester at the Bowater, Inc. kraft pulp mill in Thunder Bay, Ontario, over a period of approximately nineteen days, as measured by FT-IR and by manual titration.

A multi-component PLS model was generated for white liquor using as many as 278 near infrared absorbance spectra of synthetic and real white liquor samples in the calibration training set. These training samples included variations in the concentration of EA, sulphide, carbonate, and chloride, as well as variations in the temperature of the sample liquor and the reference water. This model was applied to spectra collected by an on-line FT-IR spectrometer (Bomem, Hartmann & Braun, Workir 160) at the Bowater, Inc. kraft pulp mill in Thunder Bay, Ontario. FIG. 13 is a plot of the EA concentration of white liquor being fed into the B digester at this mill over a period of approximately nineteen days, as measured by FT-IR and by manual titration with hydrochloric acid.

Figure 14:
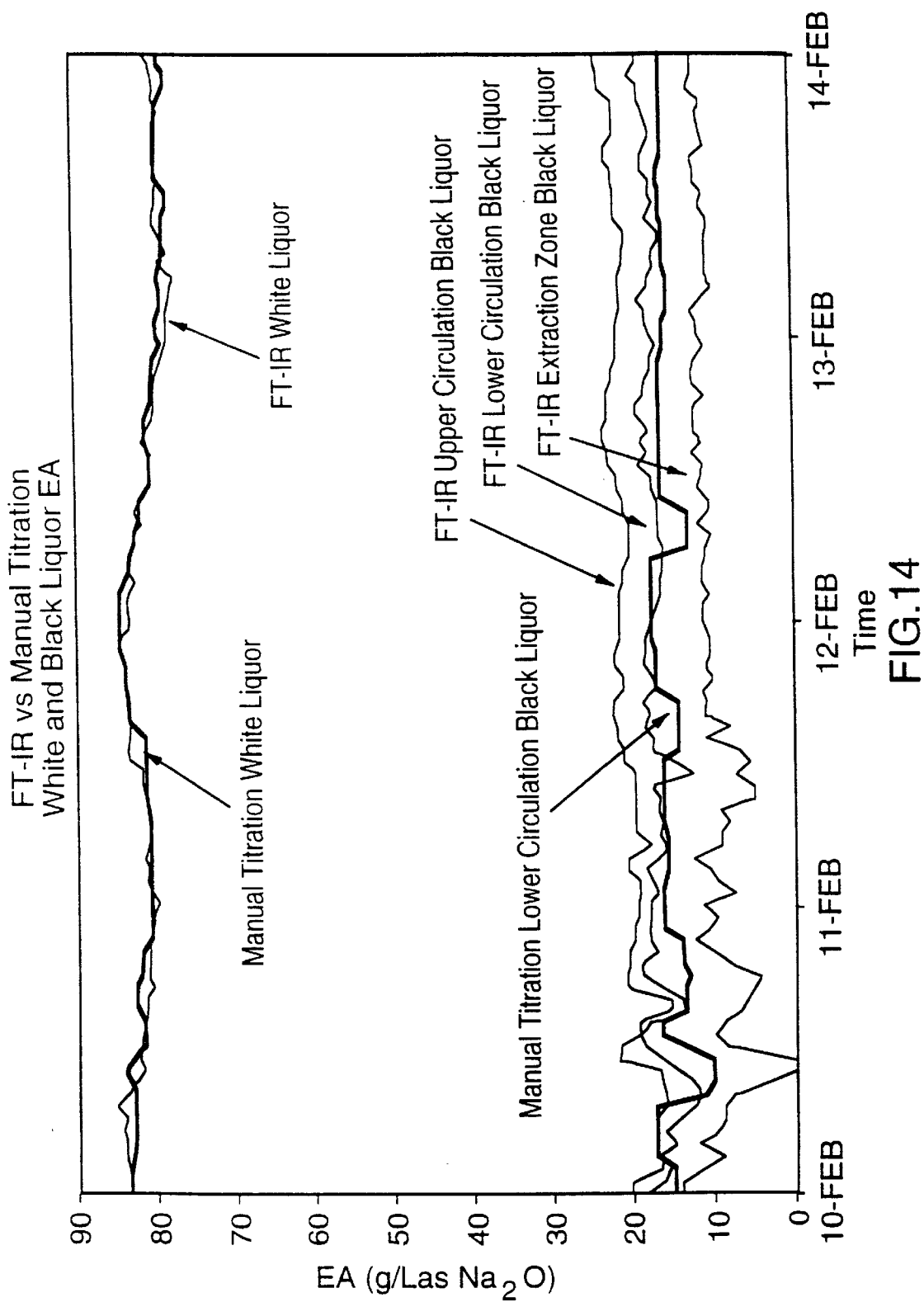
FIG. 14 is a plot of the concentration of white liquor, upper circulation black liquor, lower circulation black liquor, and extraction zone black liquor at the Bowater, Inc. kraft pulp mill in Thunder Bay, Ontario, over a period of approximately four days, as measured by FT-IR and manual titration.

A one-component PLS model was generated for black liquor using as many as 457 near infrared absorbance spectra of synthetic and real white and black liquor samples in the calibration training set. FIG. 14 is a plot of the concentration of white liquor, upper circulation black liquor, lower circulation black liquor, and extraction zone black liquor at the Bowater, Inc. kraft pulp mill in Thunder Bay, Ontario. Data is shown for a period of approximately four days, as measured by FT-IR and by manual titration with hydrochloric acid. A shorter time period is presented for graphical clarity. Manual titration data is only collected by the mill personnel for EA on white liquor and lower circulation black liquor. This example demonstrates (1) long term correlation with manual titration results, (2) no instrumental drift, (3) no optical degradation, (4) accurate measurement in the presence of gaseous bubbles and solids, and (5) no plugging of the flow cell by solids or fibres since a large pathlength flow cell was used (8 mm) as stated in the present invention.

Thus, a rapid method is provided for the control of a cellulosic pulp manufacturing process via on-line measurement of chemical concentration parameters in process liquor streams with near infrared radiation. The method eliminates the need for (i) manual sampling, (ii) frequent equipment maintenance, (iii) a dedicated instrument at each sampling point, (iv) compensation for instrumental drift, and (v) an environmentally controlled spectrometer housing near the sampling location(s). The method includes the steps of (i) withdrawing samples of a process liquor stream from a cellulosic pulp manufacturing process, (ii) subjecting the samples to near-infrared spectrophotometry over a predetermined range of wavenumbers so as to produce spectral measurements which determine the concentrations of different combinations of chemical components, (iii) correlating by multivariate calibration the relationships between the spectral measurements of unknown samples and the spectral variations shown by different combinations of chemical components of the process liquor so that concentration parameters can be accurately determined for typical levels of chemical components present in the process liquor, and (iv) controlling at least one process parameter so as to obtain optimal operation of the cellulosic pulp manufacturing process.

EXAMPLE 5

Figure 15:
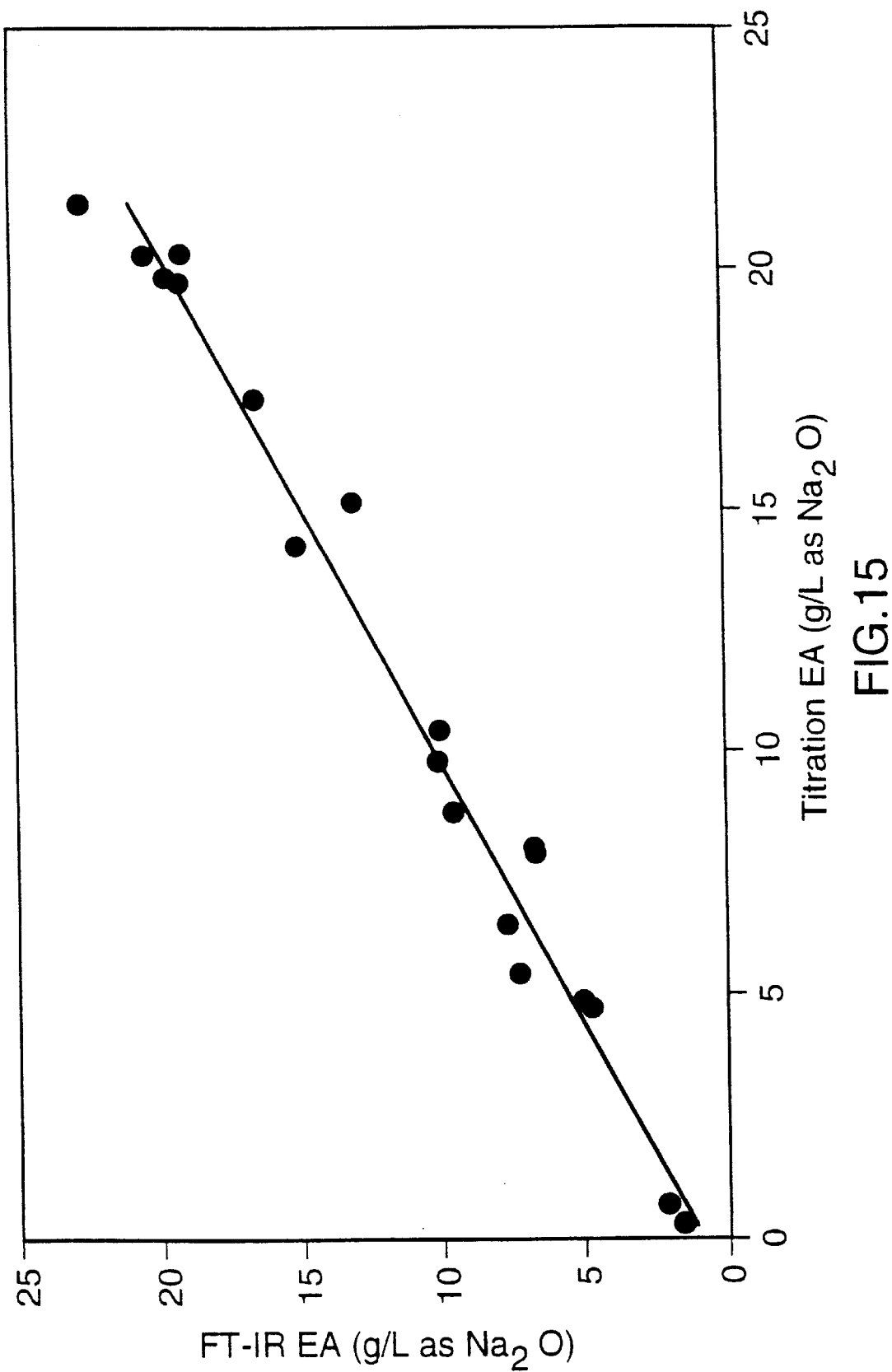
FIG. 15 is a calibration graph concerning effective alkali.
Figure 16:
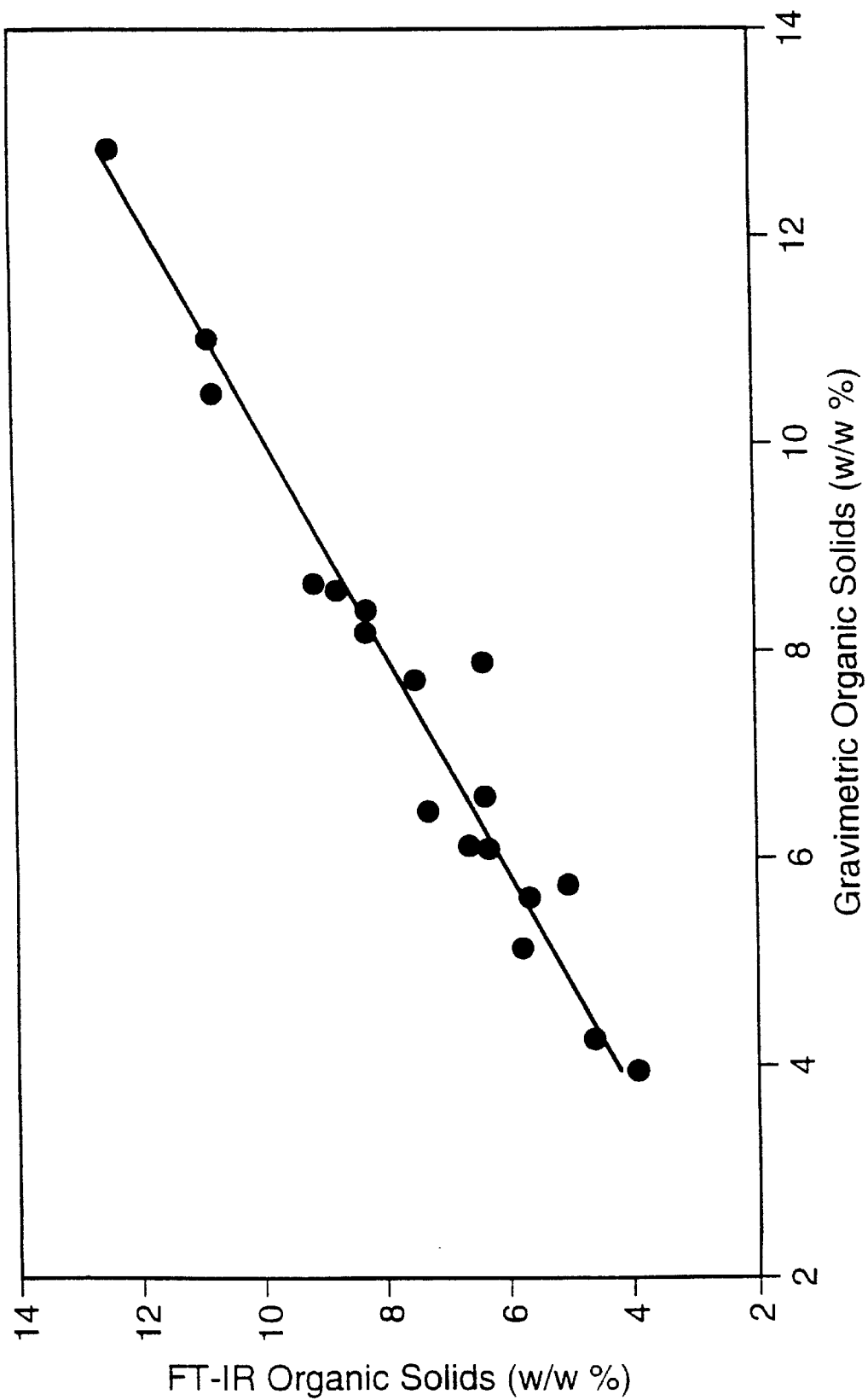
FIG. 16 is a calibration graph concerning organic solids.
Figure 17:
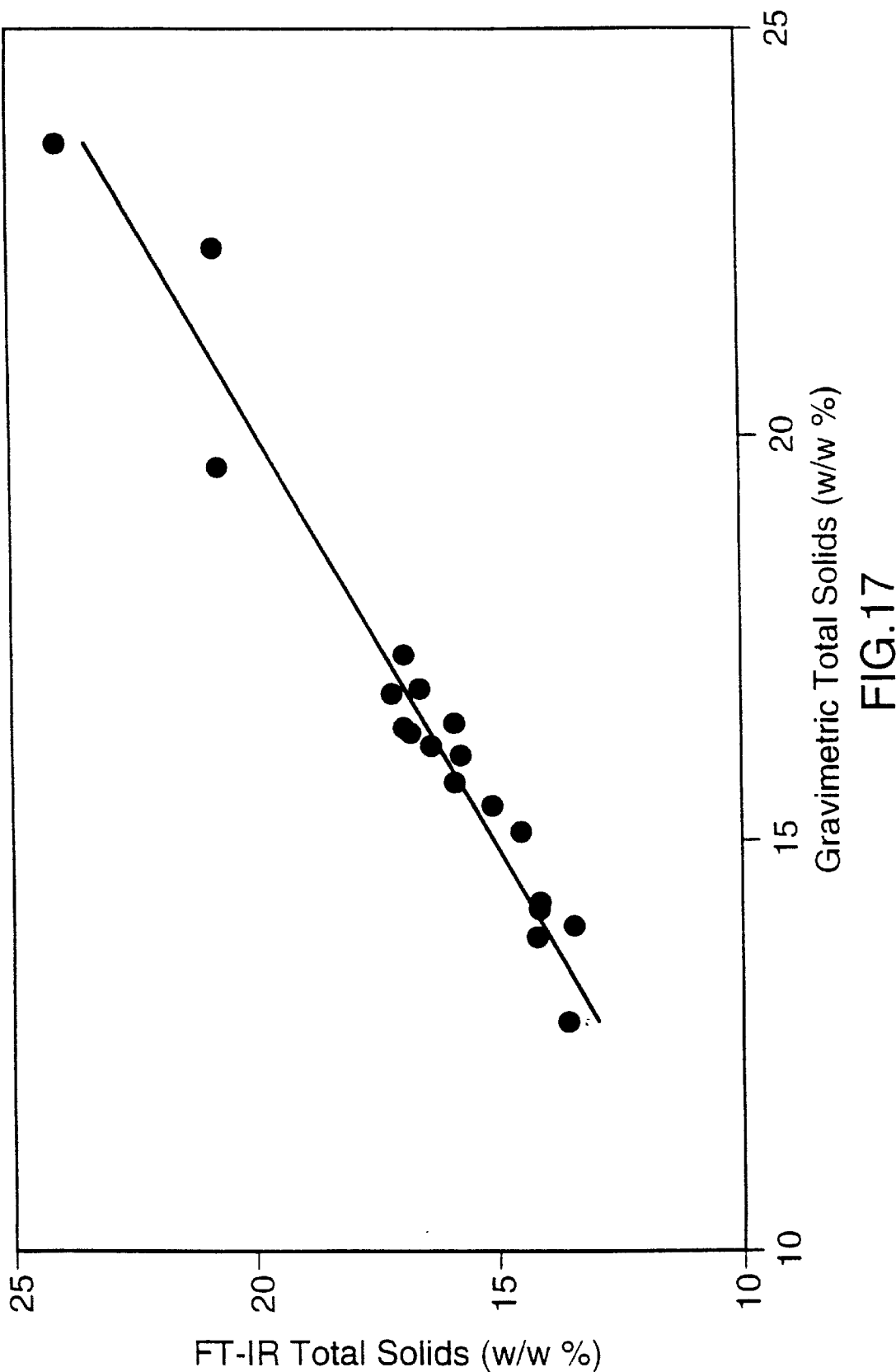
FIG. 17 is a calibration graph concerning total solids.

A three-component PLS calibration was performed on the infrared spectra of a set of nineteen black liquors collected from several kraft pulp mills across Canada. A calibration model was constructed that is capable of predicting (1) effective alkali (EA) concentrations, (2) organic solids content and (3) total solids content. Table III lists the concentrations of the effective alkali (g/L as Na$_2$O), organic solids (w/w %), and total solids (w/w %) content o f these black liquor samples. The EA was determined by automatic titration with 1.00 N HCl to an endpoint determined by the inflection of a pH versus volume of acid added curve between pH 11.0 and 11.5, in the presence of 0.1 M Na$_2$CO$_3$. The total solids content was determined gravimetrically by drying 25.00 mL of the black liquor sample to a constant weight in a drying oven at 105±2° C. the organic solids content was also determined gravimetrically by subtracting the mass obtained by igniting to a constant weight the remaining dried solids at 550±25° C. from the total solids content. The spectra were measured at a constant temperature of 30° C. using a pathlength of 8 mm. The spectral region chosen for building the model was from 11533 to 7382 wavenumbers (cm$^{-1}$) for all three components. A pre-processing step of calculating a second derivative function with a 31-point Savitzky-Golay smoothing procedure was performed on the spectra prior to running the calibration. A total of three PLS factors were used for the predictions. The calibration graphs are shown in FIG. 15 (effective alkali), FIG. 16 (organic solids) and FIG. 17 (total solids), all of which demonstrate good agreement between the FT-IR and the reference method values. Since total solids content is equal to the sum of the organic solids content and the inorganic solids content, the inorganic solids content can be calculated by determining the values of the organic and the total solids contents from the liquor. From these results, it is possible to calculate effective alkali, organic solids, inorganic solids, and total solids content.

TABLE III

Compositions of mill black liquor samples used for the three-component PLS calibration

| Sample No. | Effective Alkali (g/L as Na$_2$O) | Organic Solids (w/w %) | Total Solids (w/w/ %) |
|---|---|---|---|
| 1 | 0.3 | 8.6 | 17.2 |
| 2 | 20.2 | 5.1 | 15.6 |
| 3 | 21.3 | 5.7 | 16.4 |
| 4 | 5.4 | 6.4 | 14.2 |
| 5 | 8 | 8.3 | 16.2 |
| 6 | 7.9 | 8.1 | 16.3 |

TABLE III-continued

Compositions of mill black liquor samples used
for the three-component PLS calibration

| Sample No. | Effective Alkali (g/L as $Na_2O$) | Organic Solids (w/w %) | Total Solids (w/w/ %) |
|---|---|---|---|
| 7 | 19.6 | 6.1 | 17.7 |
| 8 | 4.7 | 7.7 | 15.4 |
| 9 | 20.2 | 3.9 | 13.9 |
| 10 | 4.8 | 6.1 | 12.7 |
| 11 | 17.2 | 6.1 | 16.1 |
| 12 | 0.7 | 8.5 | 16.8 |
| 13 | 9.8 | 12.8 | 23.6 |
| 14 | 10.4 | 11.0 | 22.3 |
| 15 | 15.1 | 5.6 | 13.8 |
| 16 | 6.4 | 10.4 | 19.6 |
| 17 | 14.2 | 6.5 | 16.0 |
| 18 | 8.7 | 7.8 | 15.0 |
| 19 | 19.7 | 4.2 | 14.1 |

EXAMPLE 6

To investigate whether sulphate and/or thiosulphate could be measured in the presence of hydroxide and carbonate, 11 liquor solutions were measured which represent typical oxidized sulphur concentrations in an oxidized or super-oxidized white liquor. All near infrared spectra (from 4000 to 14000 $cm^{-1}$) were collected at 30.0±0.5° C. in a temperature-controlled circulation loop using an 8 mm pathlength flow cell. The flow cell was connected to a spectrometer (Networkir, Bomem Inc., Quebec, Canada) using two 300 μm diameter fiber-optic cables that were each 10 m long. A short-range InGaAs detector was used with a first stage gain of 2 and a second stage gain of 16. There are 200 co-added scans at 16 $cm^{-1}$ resolution collected for each solution. The concentrations of the components in each solution are shown in Table IV.

TABLE IV.

Concentration of EA, carbonate, sulphate and thiosulphate in 11 solutions.

| Solution | EA (g/L as $Na_2O$) | Carbonate (g/L as $Na_2O$) | Sulphate (g/L as $Na_2SO_4$) | Thiosulphate (g/L as $Na_2S_2O_3$) |
|---|---|---|---|---|
| 1 | 80 | 15 | 0 | 0 |
| 2 | 80 | 15 | 5 | 0 |
| 3 | 80 | 15 | 10 | 0 |
| 4 | 80 | 15 | 15 | 0 |
| 5 | 80 | 15 | 50 | 0 |
| 6 | 80 | 15 | 100 | 0 |
| 7 | 80 | 15 | 0 | 5 |
| 8 | 80 | 15 | 0 | 10 |
| 9 | 80 | 15 | 0 | 15 |
| 10 | 80 | 15 | 0 | 50 |
| 11 | 80 | 15 | 0 | 100 |

Figure 18:
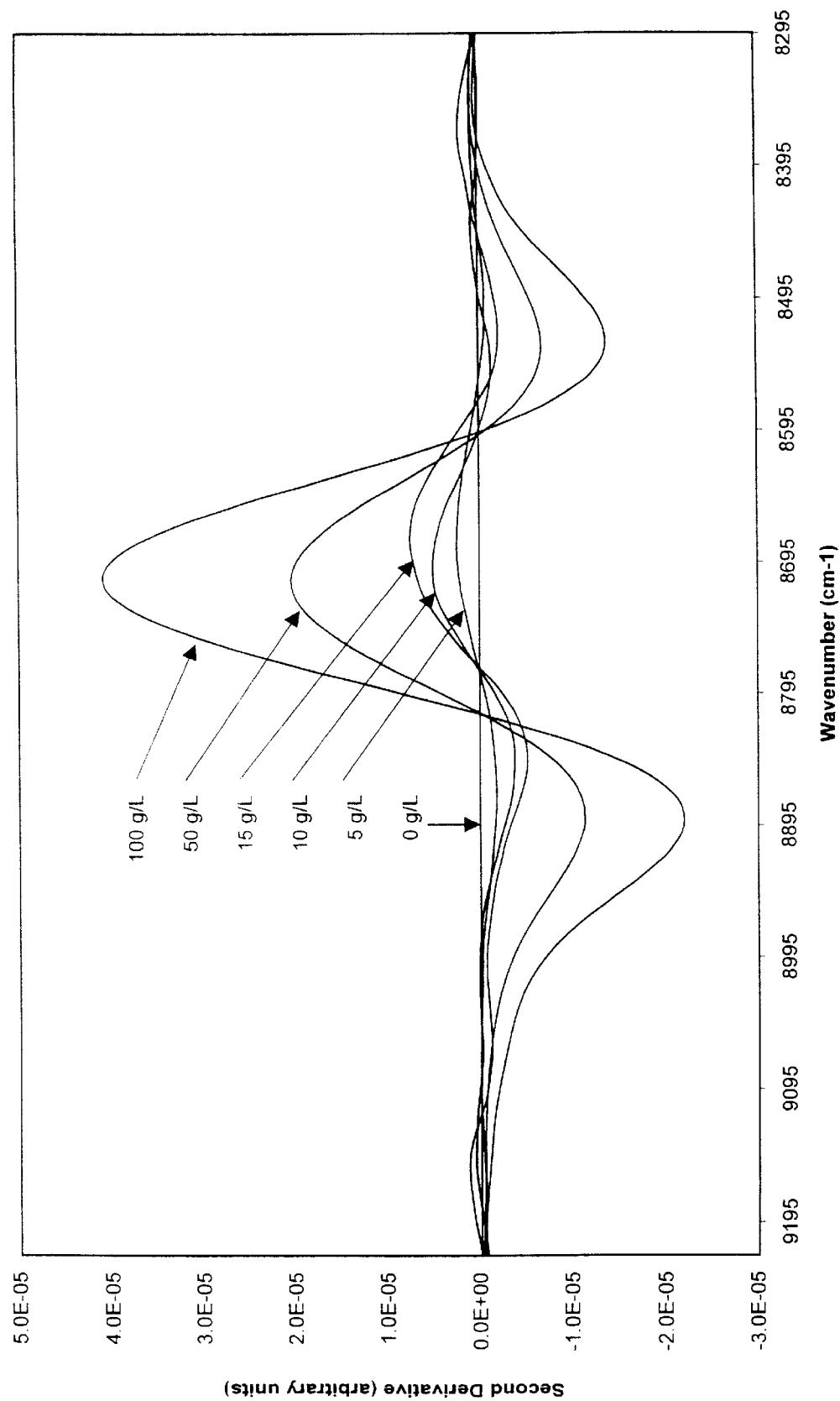
FIG. 18 is a graph of second derivative spectra versus wavenumber (reciprocal centimeters) demonstrating the changes in the near infrared spectrum of water due to sodium sulphate.
Figure 19:
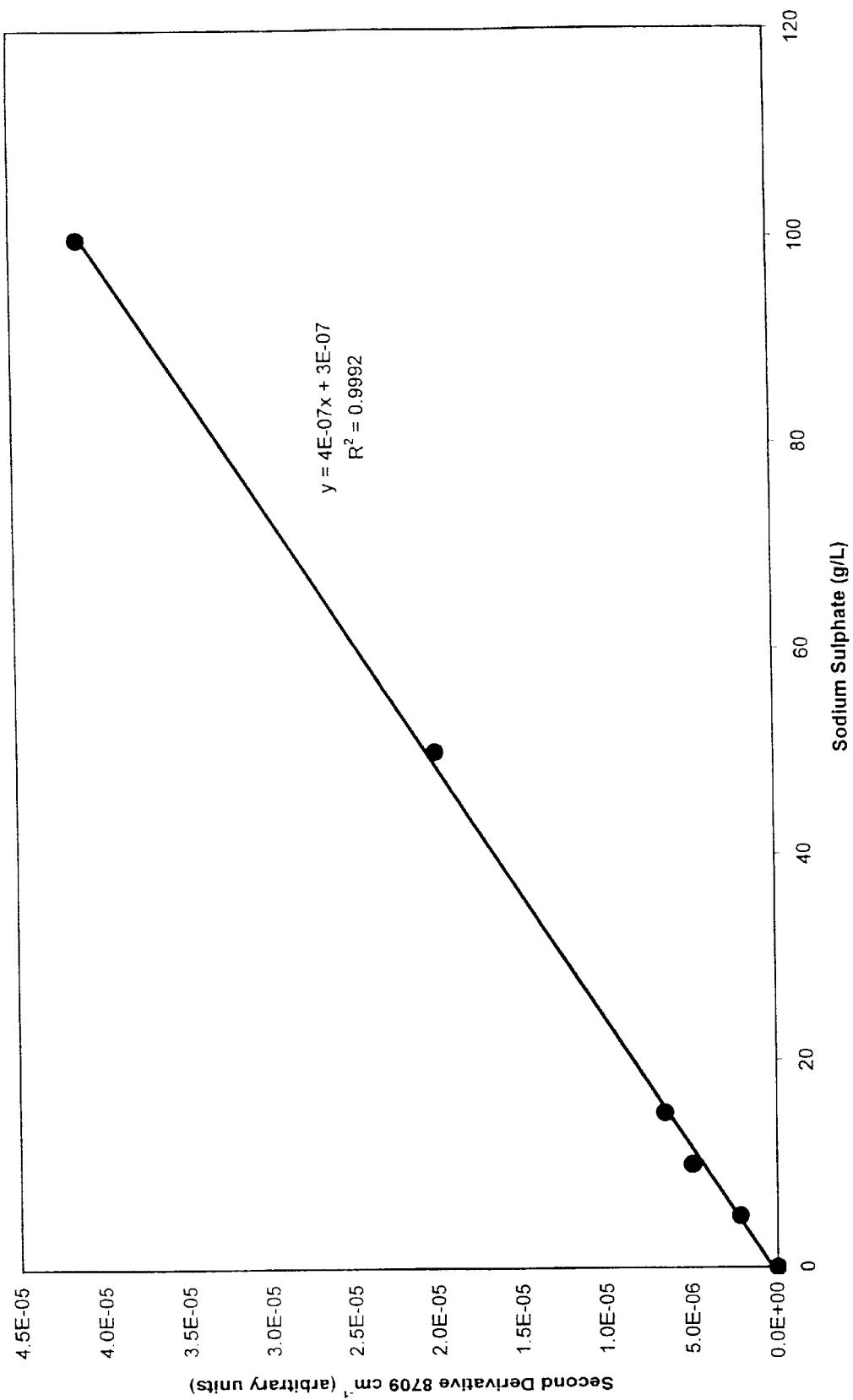
FIG. 19 is a single-wavenumber calibration graph taken at 8709 $cm^{-1}$ for sodium sulphate.

The sample matrix in all solutions contains 80 g/L EA as $Na_2O$ and 15 g/L $Na_2CO_3$ as $Na_2O$ (Solution 1). This solution was used as a reference for absorbance calculations, so that all influences on the liquor spectrum other than the sulphate and thiosulphate concentrations were effectively eliminated for the purposes of this example. A 41-point Savitzky-Golay second derivative function was then applied to the absorbance spectra, and was followed by a 21-point Savitzky-Golay smoothing function. The second derivatives of the absorbance spectra for solutions 1 through 6 are shown in FIG. 18, and a single wavelength calibration for sodium sulphate at 8709 $cm^{-1}$ is shown in FIG. 19.

Figure 20:
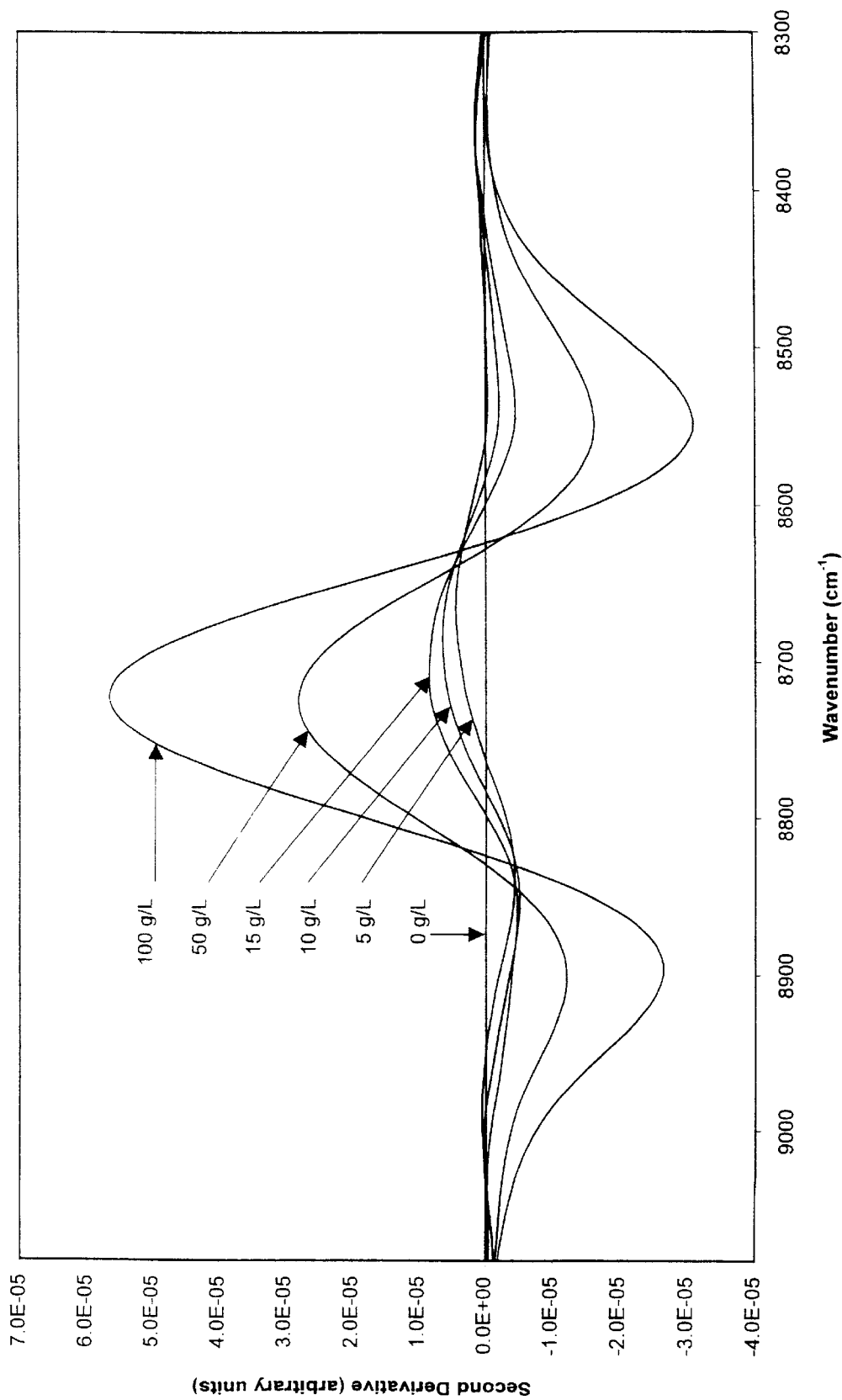
FIG. 20 is a graph of second derivative spectra versus wavenumber (reciprocal centimeters) showing the changes in the near infrared spectrum of water due to sodium thiosulphate.
Figure 21:
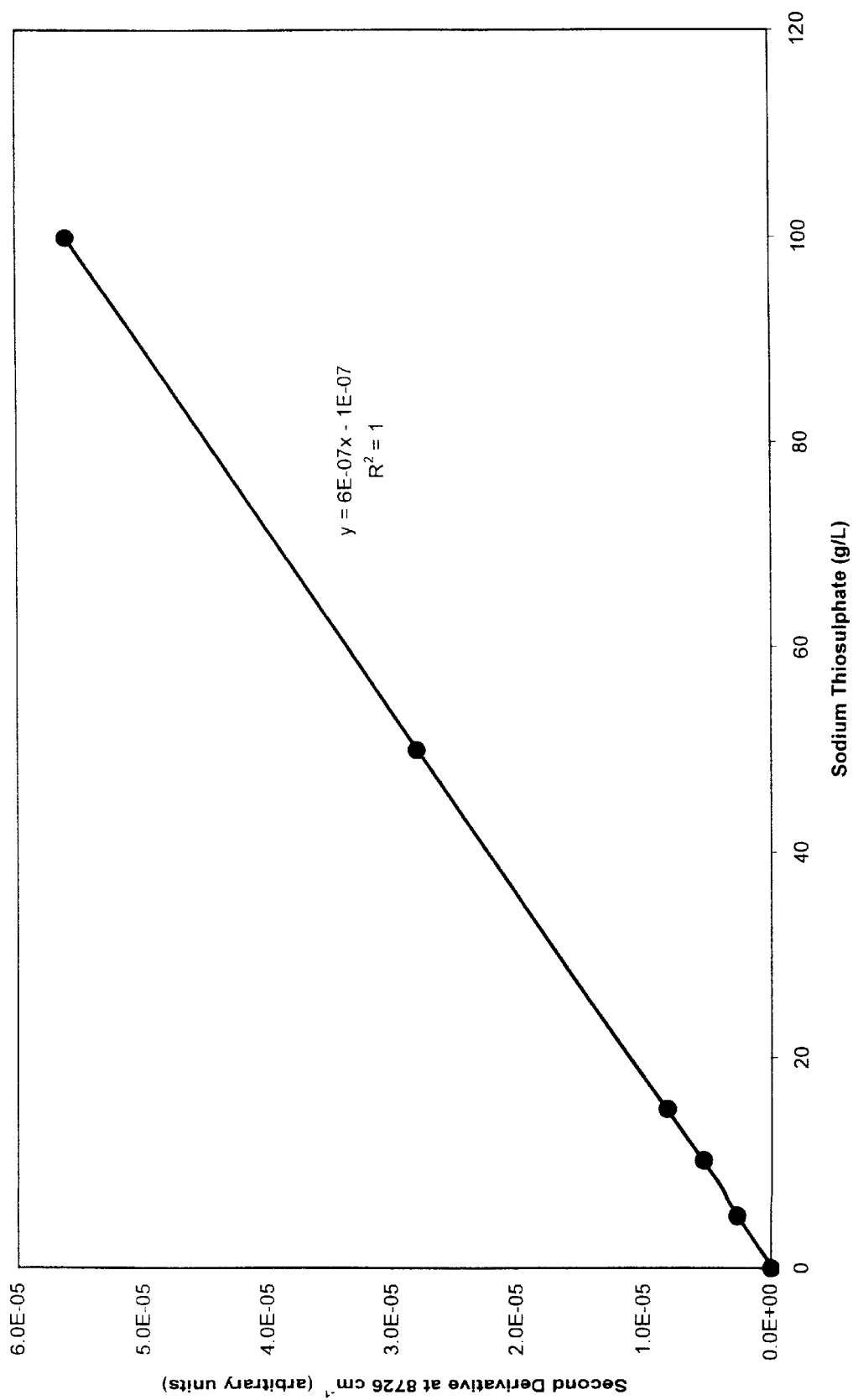
FIG. 21 is a single-wavenumber calibration graph taken at 8726 $cm^{-1}$ for sodium thiosulphate.

Likewise, the second derivatives of the absorbance spectra for solutions 7 through 11 are shown in FIG. 20, and a single wavelength calibration for sodium sulphate at 8726 $cm^{-1}$ is shown in FIG. 21. This demonstrates the ability to measure sodium sulphate and sodium thiosulphate in the presence of sodium hydroxide and sodium carbonate in oxidized white liquors and super-oxidized white liquors.

EXAMPLE 7

Figure 22:
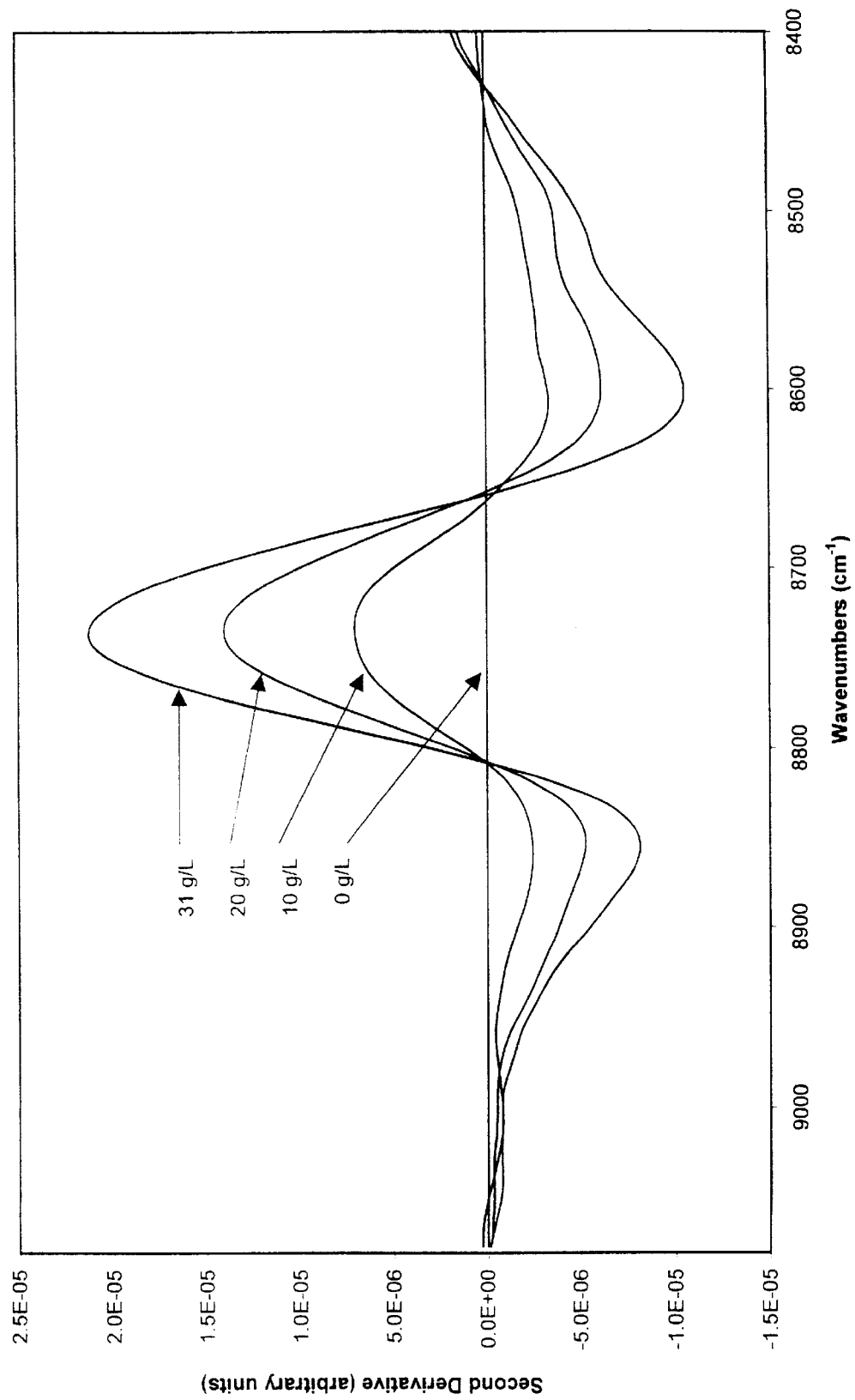
FIG. 22 is a graph of second derivative spectra versus wavenumber (reciprocal centimeters) showing the changes in near infrared region due to polysulphide when using a typical white liquor solution as a reference.
Figure 23:
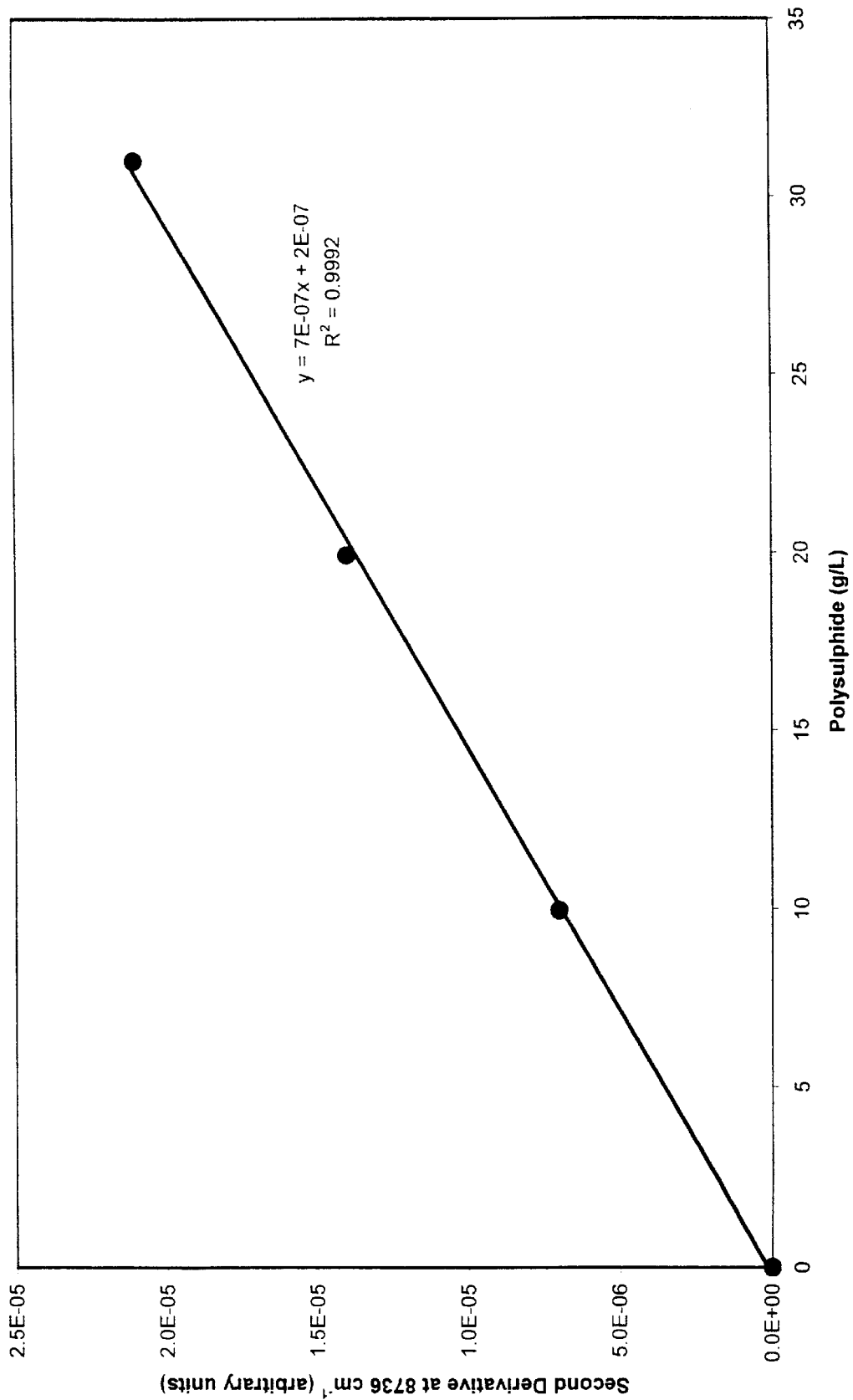
FIG. 23 is a single-wavenumber calibration graph taken at 8736 cm$^{-1}$ for polysulphide.

All spectra were measured at 21.2° C. on a Bomem 154 spectrometer (Bomem Inc., Quebec, Canada) with the use of an 8 mm variable-pathlength flow-cell. A 5 m length of fiber-optic cable connects the flow-cell and the spectrometer, which is equipped with an InAs detector. All spectra were collected with 8 $cm^{-1}$ resolution. Prior to processing, the absorbance spectra of all single-beam spectra were calculated using a background reference spectrum of white liquor containing an effective alkali of 80 g/L (as $Na_2O$), a sulphide concentration of 30 g/L (as $Na_2O$) and a carbonate concentration of 12 g/L (as $Na_2O$). In this way, all influences on the liquor spectrum other than the polysulphide concentration were effectively eliminated for the purposes of this example. A 41-point Savitzky-Golay second derivative function was then applied to the absorbance spectra, and was followed by a 21-point Savitzky-Golay smoothing function. The results are shown in FIG. 22 for polysulphide liquors containing 10, 20 and 31 g/L (as S). A clear positive correlation can be established between the second-derivative absorbance and the polysulphide concentration around 8736 $cm^{-1}$. A calibration graph is shown in FIG. 23 based on the second-derivative absorbance at 8736 $cm^{-1}$. The fit is very linear ($r^2$=0.9992), with a slope of $7 \times 10^{-7}$ and an intercept of $2 \times 10^{-7}$.

EXAMPLE 8

Figure 24:
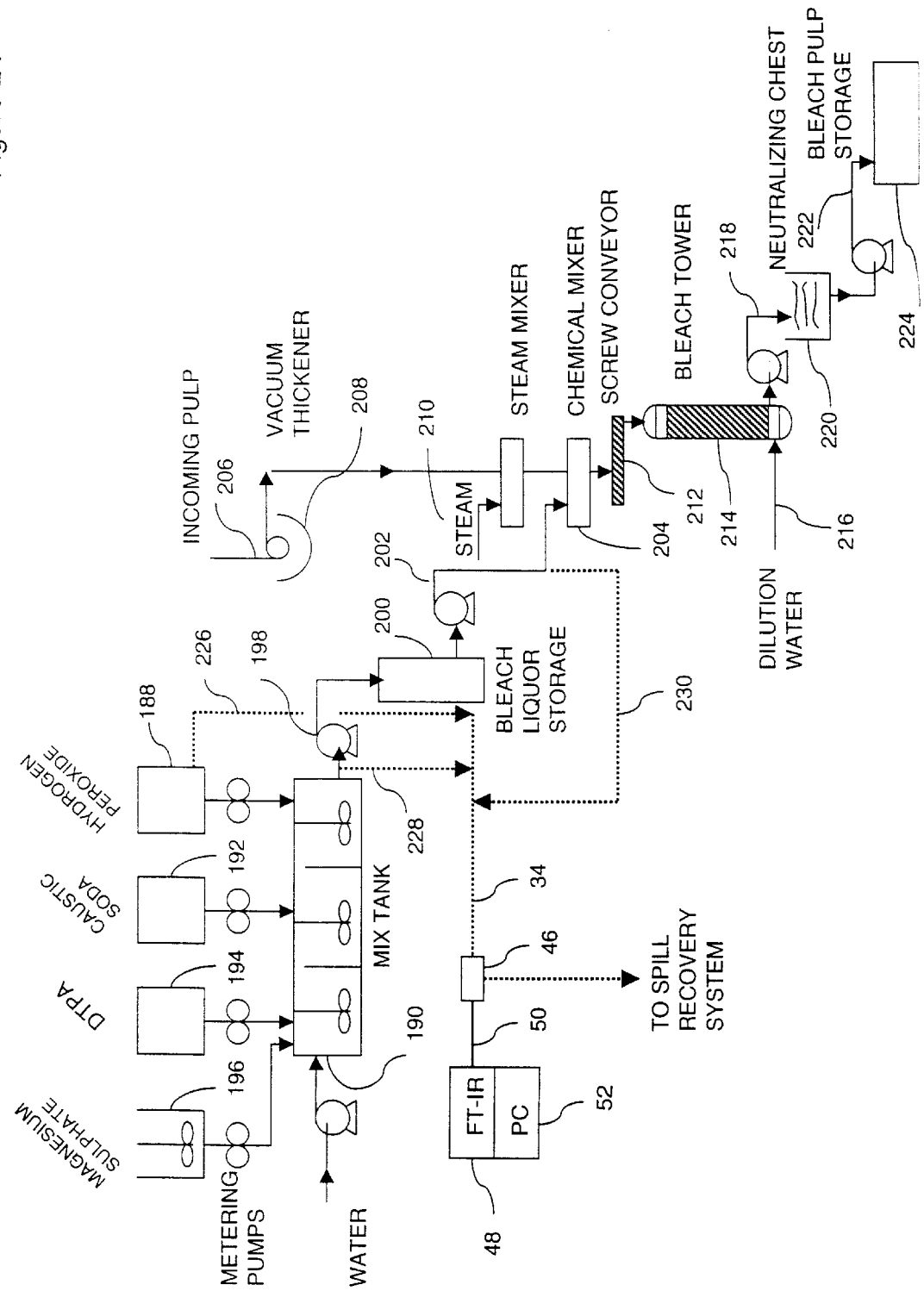
FIG. 24 is a diagrammatic view of a bleach plant which utilizes hydrogen peroxide, complete with sensing and control apparatus according to one embodiment of the present invention.

Referring to FIG. 24, a concentrated solution of hydrogen peroxide (typically 30 to 35% weight by volume) is fed from a holding tank 188 into a mixing tank 190, in conjunction with varying amounts of (a) caustic soda fed from a second holding tank 192, (b) DTPA (a chelating agent) fed from a third holding tank 194, and (c) magnesium sulfate fed from a fourth holding tank 196. After mixing, the resulting bleach liquor is pumped through line 198 and temporarily stored before use in a storage tank 200. The bleach liquor is then pumped through line 202 to a chemical mixer 204, merged with the partially bleached pulp 206, which has been previously concentrated in a vacuum thickener 208, and mixed with steam 210. The pulp is then carried through a screw conveyor 212 to the bleach tower 214. After bleaching, the pulp is then diluted with water 216 and pumped through line 218 to a neutralizing chest 220, prior to being transported through line 222 to a storage tank 224. Liquor samples are taken at (a) sample withdrawing point 226 from holding tank 188, (b) sample withdrawing point 228 in line 198, and (c) sample withdrawing point 230 in line 202. The samples are fed through a 1.25-cm diameter conduit 34, optionally merged with other optional streams 226, 228, and 230 through either transmittance-mode or reflectance-mode flow cell 46, well-known in the art. Infrared light from an infrared source which is integral to a Fourier-transform spectrometer 48 is brought to the flow-cell 46 by means of a direct optical coupling with mirrors or by a fiber optic cable 50. Some of the infrared light is absorbed by the bleaching liquor and the residual light is returned to the Fourier-transform spectrometer by means of either a direct optical coupling with mirrors or by a second fiber optic cable 50. The spectrometer 48 records the near-infrared single-beam spectrum of the bleaching liquor. Readings from the spectrometer 48 are transferred to a computer 52, which calculates the hydrogen peroxide concentration of the bleach liquor with the use of a PLS multi-component calibration model.

Four solutions of hydrogen peroxide and sodium silicate (added as a stabilizer) in water were generated according to Table V. All near infrared spectra (from 4000 to 14000 cm$^{-1}$) were collected at 30.0±0.5 C in a temperature-controlled circulation loop using an 8 mm pathlength flow cell. The flow cell was connected to a spectrometer (Networkir, Bomem Inc., Quebec, Canada) using two 300 μm diameter fiber-optic cables that were each 10 m long. A short-range INGaAs detector was used with a first stage gain of 2 and a second stage gain of 16. A total of 200 co-added scans were collected for each solution at a resolution of 16 cm$^{-1}$.

TABLE V.

Concentrations of hydrogen peroxide and sodium silicate in four measured solutions.

| Solution | Hydrogen Peroxide (% w/w) | Sodium Silicate (g/L) |
|---|---|---|
| 1 | 0.0 | 3.0 |
| 2 | 5.2 | 3.0 |
| 3 | 9.9 | 3.0 |
| 4 | 14.0 | 3.0 |

Figure 25:
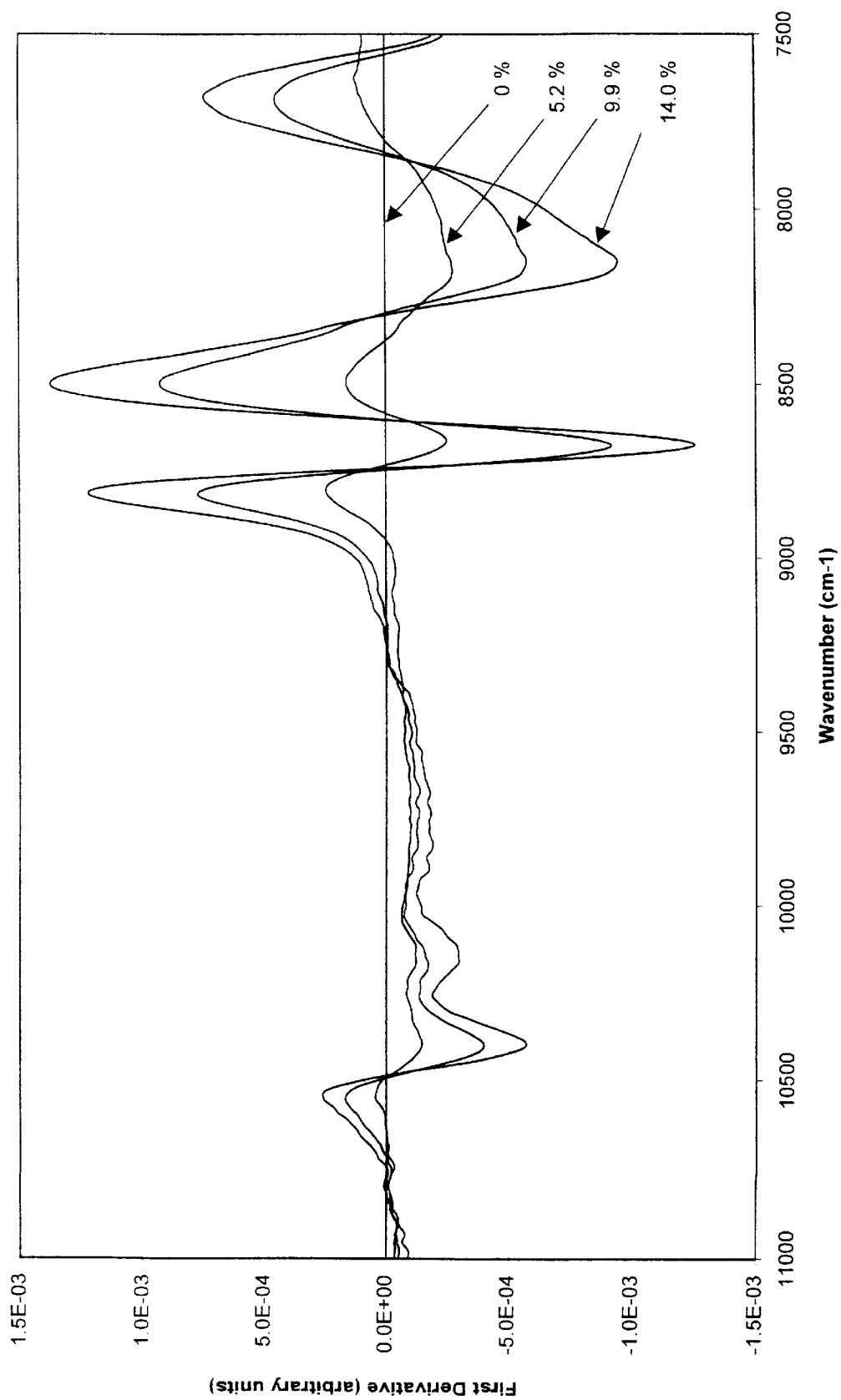
FIG. 25 is a graph of first derivative spectra taken versus wavenumber (reciprocal centimeters) showing the changes in the near infrared spectrum of water due to hydrogen peroxide.
Figure 26:
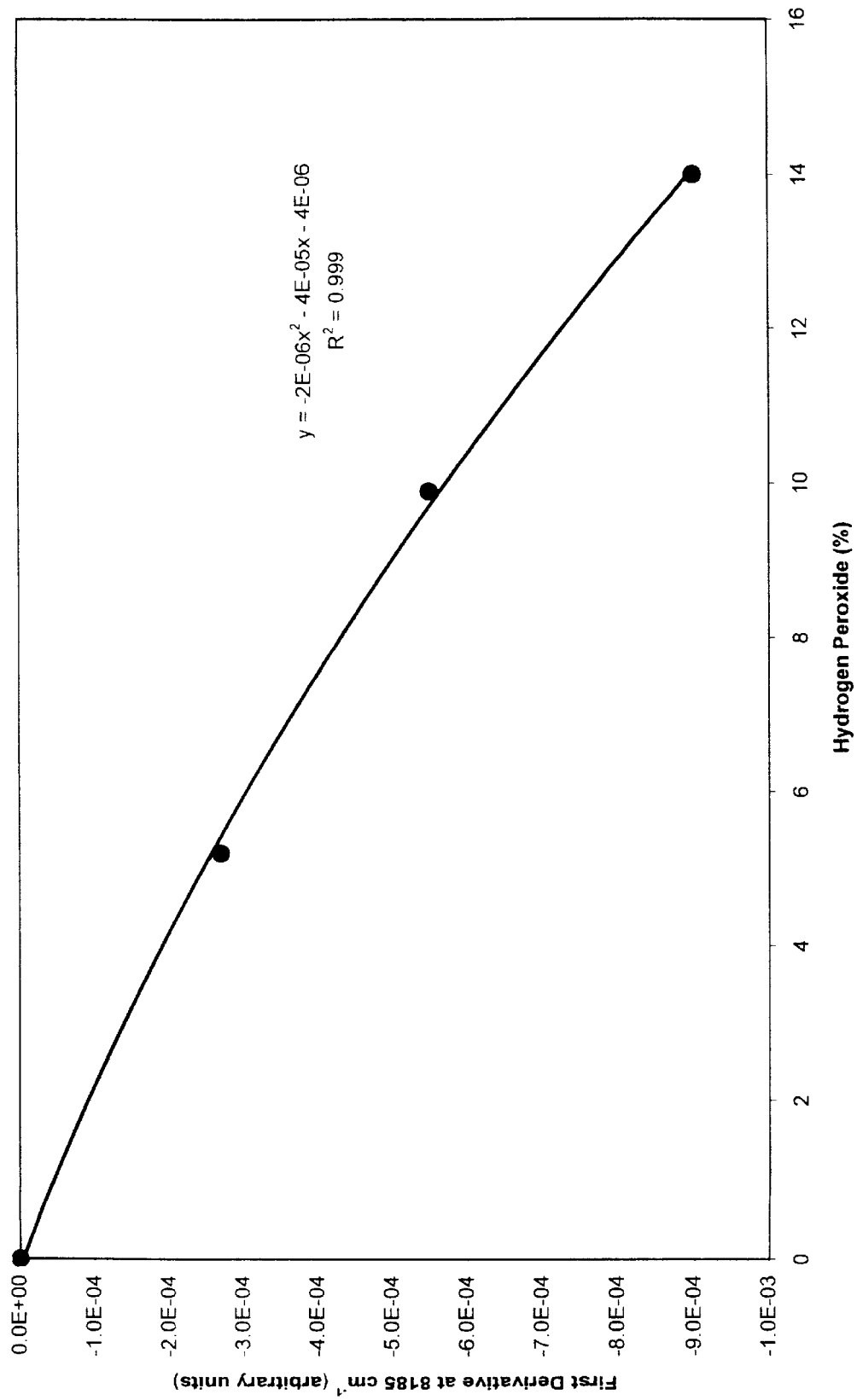
FIG. 26 is a single-wavenumber calibration graph taken at 8185 cm$^{-1}$ for hydrogen peroxide.

Solution 1 was used as a background reference solution for calculating the absorbance spectrum of all four solutions. A 41-point Savitzky-Golay first derivative function was then applied to all four absorbance spectra, which are shown in FIG. 25. A single wavelength calibration for hydrogen peroxide at 8185 cm$^{-1}$ was readily modeled by a second-order polynomial with a regression coefficient of 0.9990. This demonstrates the ability to measure hydrogen peroxide in the presence of other additives such as sodium silicate in bleach-plant process streams.

EXAMPLE 9

Figure 27:
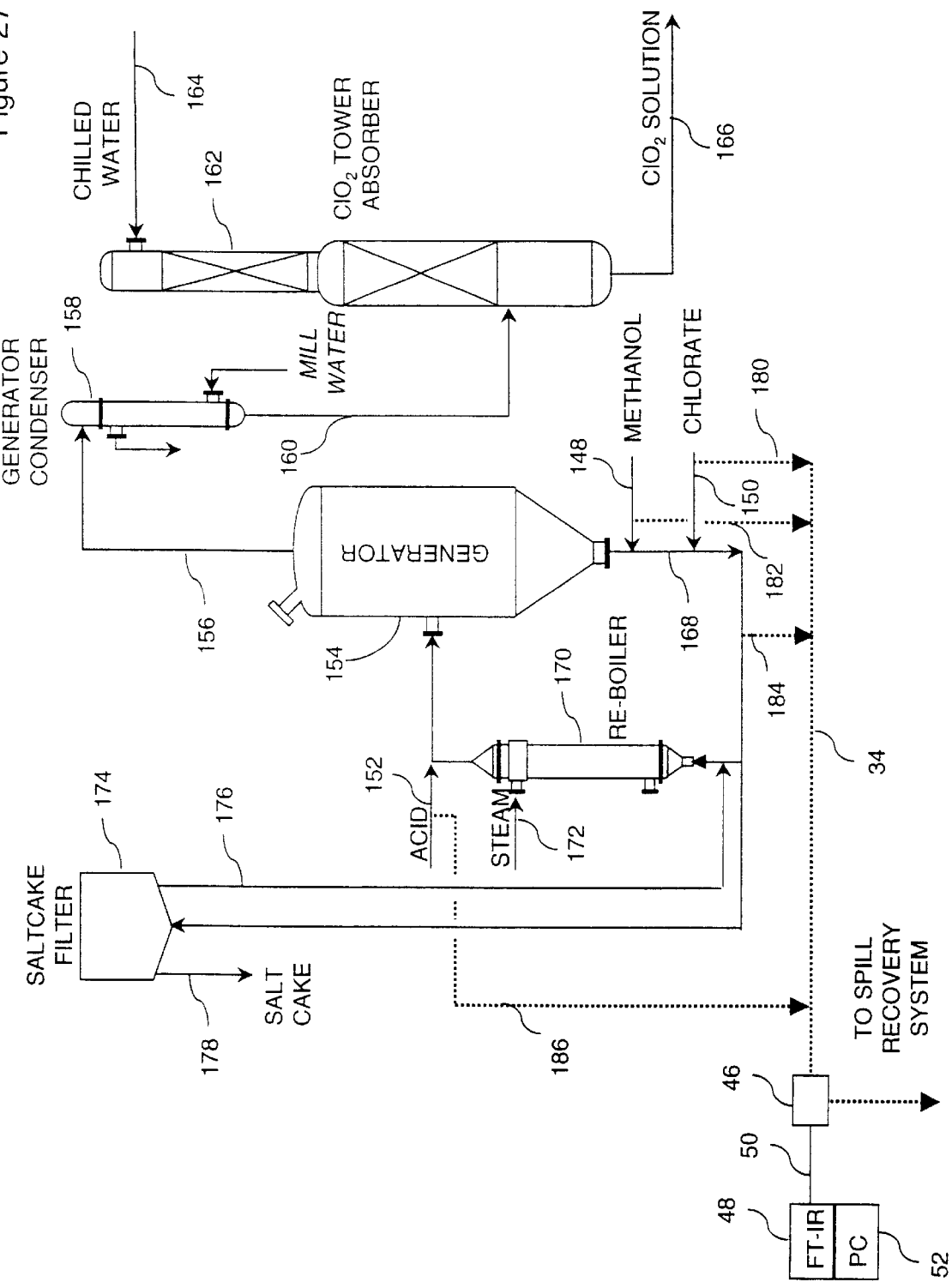
FIG. 27 is a diagrammatic view of a chlorine dioxide generator, complete with sensing and control apparatus according to one embodiment of the present invention.

Referring to FIG. 27, methanol 148, sodium chlorate 150, and sulfuric acid 152 solutions are fed into the generator 154 where the sodium chlorate is reduced to form chlorine dioxide gas 156. Chlorine dioxide gas and steam 156 passes from the generator to the condenser 158, which cools the gas. The cooled chlorine dioxide gas 160 passes into the chlorine dioxide absorber 162 where the gas is absorbed by the chilled water 164 to form chlorine dioxide solution 166 for use in the bleach plant. Generator solution 168 is pumped through a re-boiler 170, heated by steam 172, which is used to provide the heat necessary to boil off excess water in the generator. Sodium sulfate ($Na_2SO_4$) and sodium sesquisulfate ($Na_3H(SO_4)_2$) crystals, also known as saltcake, are produced as byproducts of the chlorine dioxide generation. Generator solution 168 containing these crystals flows to a saltcake filter 174, which removes the saltcake crystals. The filtered generator solution 176 returns to the generator, while the saltcake 178 is removed from the process. The samples are fed through a 1.25-cm diameter conduit 34, optionally merged with other optional streams 180, 182, 184, and 186 through either transmittance-mode or reflectance-mode flow cell 46, well-known in the art. Infrared light from an infrared source which is integral to a Fourier-transform spectrometer 48 is brought to the flow-cell 46 by means of a direct optical coupling with mirrors or by a fiber optic cable 50. Some of the infrared light is absorbed by the chlorine dioxide solution and the residual light is returned to the Fourier-transform spectrometer by means of either a direct optical coupling with mirrors or by a second fiber optic cable 50. The spectrometer 48 records the near-infrared single-beam spectrum of the chlorine dioxide solution. Readings from the spectrometer 48 are transferred to a computer 52, which calculates the individual component concentrations of the bleaching solution, such as, sodium chlorate, sulphuric acid, and methanol with the use of a PLS multi-component calibration model.

Figure 28:
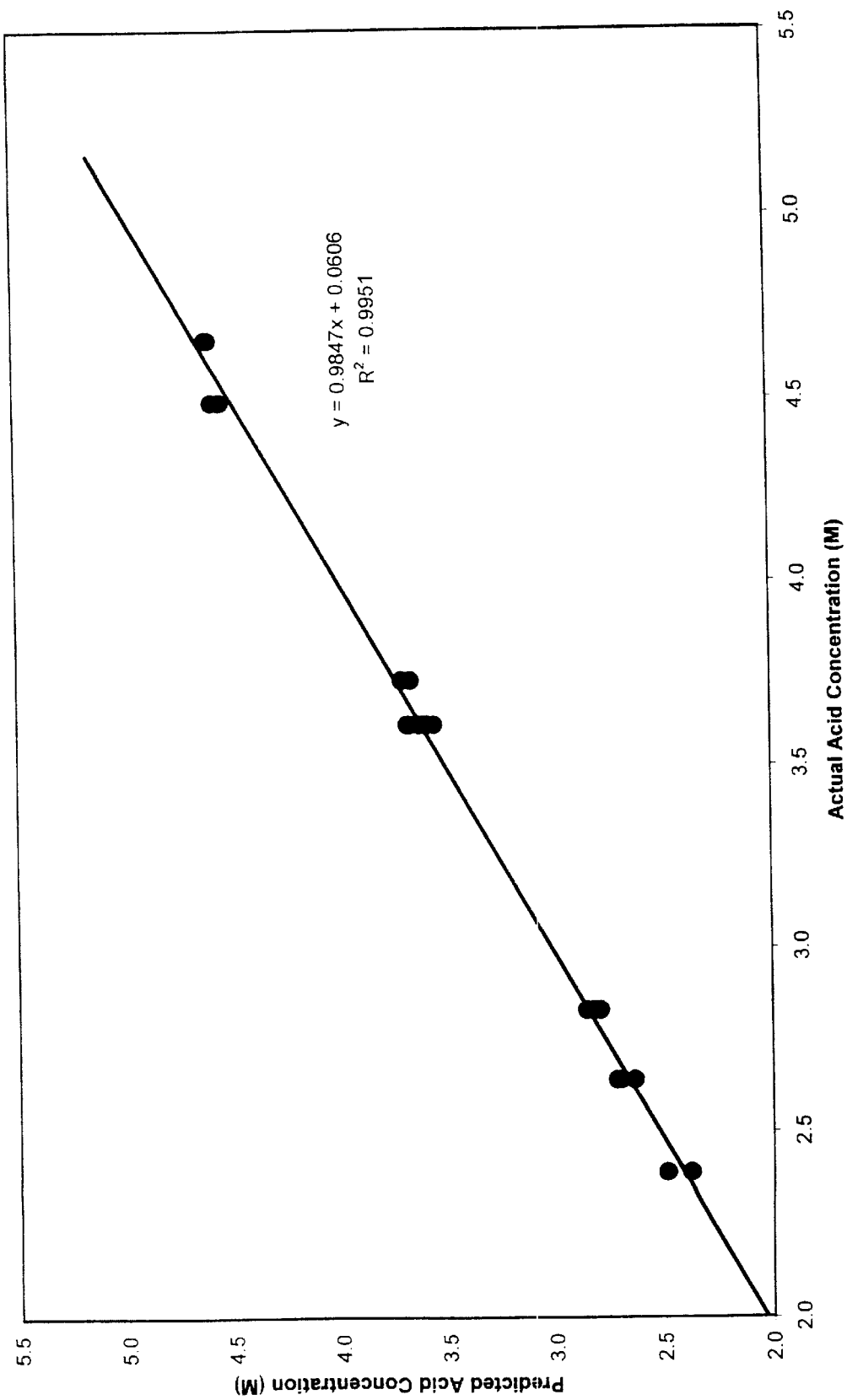
FIG. 28 is a plot of predicted versus actual sulphuric acid concentration for a typical chlorine dioxide generator solution.
Figure 29:
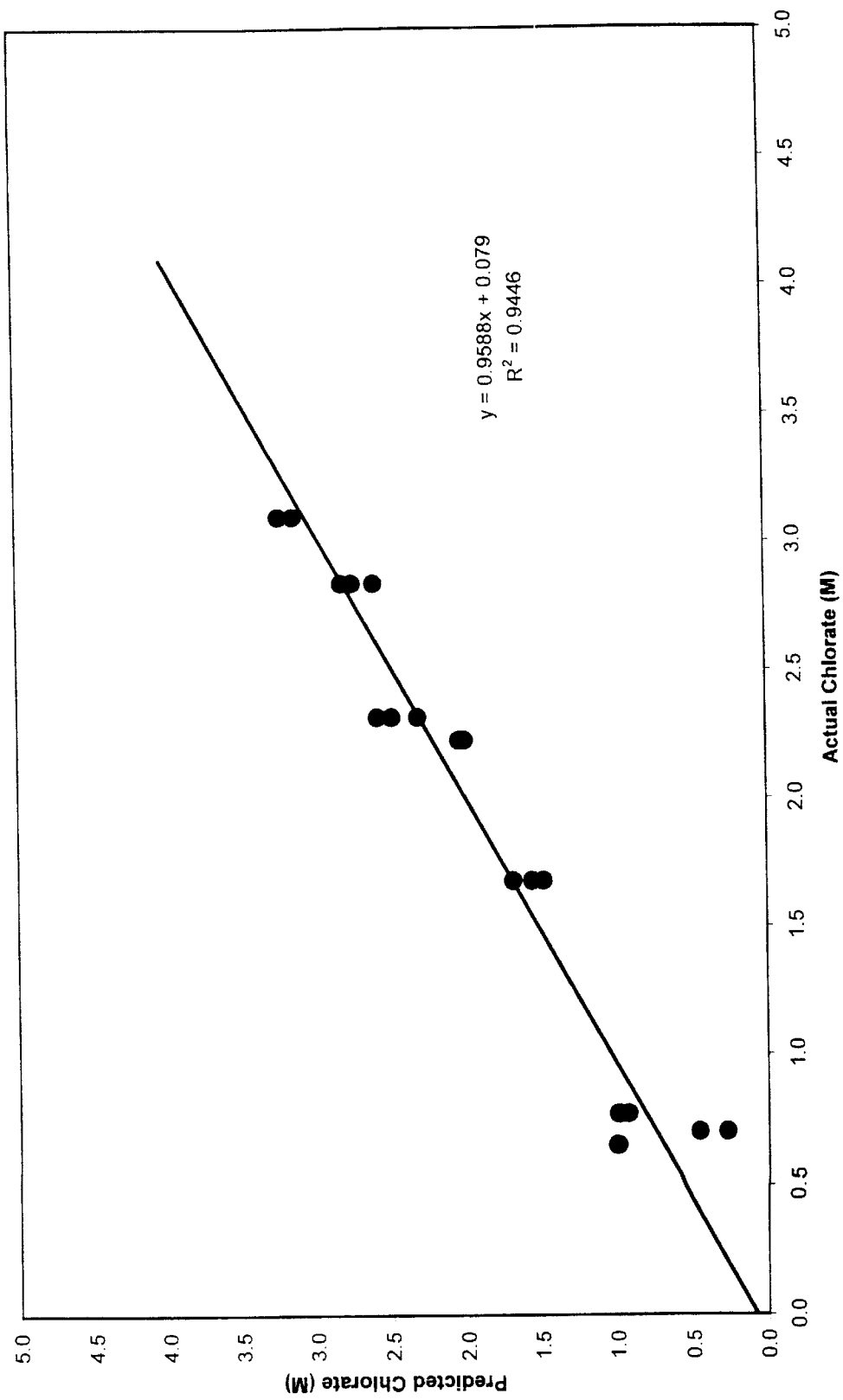
FIG. 29 is a plot of predicted versus actual chlorate concentration for a typical chlorine dioxide generator solution.

A two component PLS calibration was developed based on the set of synthetic samples listed in Table VI for the purpose of building a calibration model that is capable of determining sodium chlorate and sulphuric acid ($H^+$) concentrations. Mixtures of sulphuric acid, sodium chlorate, and sodium sulphate that are of typical chlorine dioxide generator solutions were prepared. A near infrared spectrum of each solution was collected using a Bomem MB 154 spectrometer equipped with a InAs detector set to gain C. Each spectrum is an average of 60 co-added scans with a resolution 8-cm$^{-1}$. Prior to spectral acquisition, samples were heated in a 1-cm by 1-cm cuvette to temperatures of 65, 70, and 75° C. in a regulated thermal block. The single-beam spectra were converted to absorbance spectra using a single water reference. The spectral region chosen for building the model was from 11000 to 7300 wavenumbers (cm$^{-1}$) for both components. The calibration graphs are shown in FIG. 28 (acid) and FIG. 29 (chlorate), both of which demonstrate good agreement between the actual (titration) and the predicted (FT-IR) values. Even in the presence of high levels of sodium sulphate (at or near saturation), water-band perturbations due to sodium chlorate and acid can be detected and quantified. The standard deviation of the differences between the actual and the predicted concentrations are 0.03 M for acid and 0.10 M for sodium chlorate.

From this example, it is possible to quantify the chlorine dioxide generator solutions in terms of chlorate and acid concentrations. This will allow the optimized production of chlorine dioxide from a generator by means of a feed-back and feed-forward control and strategy.

TABLE VI

Composition of synthetic chlorine dioxide solutions used for two-component calibration.

| | | Chlorate Concentration (M) | | |
|---|---|---|---|---|
| | | 0.75 | 2.25 | 4.00 |
| Acid Concentration (M) | 2.5 | Chlorate = 0.70<br>Acid = 2.39<br>T = 74.8, 70.5, 64.5 ° C. | Chlorate = 2.32<br>Acid = 2.64<br>T = 78.0, 69.5, 64.8 ° C. | Chlorate = 3.10<br>Acid = 2.83<br>T = 74.0, 69.5, 65.0 ° C. |

TABLE VI-continued

Composition of synthetic chlorine dioxide solutions used for two-component calibration.

| | Chlorate Concentration (M) | | |
|---|---|---|---|
| | 0.75 | 2.25 | 4.00 |
| 3.5 | Chlorate = 0.77<br>Acid = 3.74<br>T = 74.3, 71.5, 64.5 °C. | Chlorate = 2.23<br>Acid = 3.61<br>T=75.75, 70.5, 64.3 °C. | Chlorate = 2.54<br>Acid = 3.61<br>T = 74.0, 72.3, 64.3 °C. |
| 5.0 | Chlorate = 0.65<br>Acid = 4.66<br>T = 75.5, 70.0, 65.3 °C. | Chlorate = 1.68<br>Acid = 3.61<br>T = 75.8, 71.3, 64.0 °C. | Was not prepared |

Although this disclosure has described and illustrated certain preferred embodiments of the invention, it is to be understood that the invention is not restricted to those particular embodiments. Rather, the invention includes all embodiments which are functional or mechanical equivalents of the specific embodiments and features that have been described and illustrated.

What is claimed is:

1. A method for determining the concentration of hydrogen ion, organic anionic species and anionic species selected from the group consisting of $OH^-$, $CO_3^=$, $HS^-$, $ClO_3^-$, $SO_4^=$, $S_2O_3^=$, polysulphide and peroxide to a level of precision of about ±1 g/L species concentration in a sample pulp mill process liquor containing at least $OH^-$, $CO_3^=$ and $HS^-$, and further containing one or more components selected from the group consisting of suspended solids, suspended fibers, gaseous bubbles, lignin, hemicellulose and cellulose degradation products, fatty acids and resinous acids, said method comprising subjecting said liquor to near infrared radiation at a wavelength region of wave numbers selected from about 7,000 to 14,000 $cm^{-1}$ through a liquor path length of at least 3 mm to obtain spectral data for said liquor; obtaining comparative spectral data for said anionic species at known concentrations in aqueous solutions; and correlating by multivariate calibration the relationships between said spectral data of said sample liquor and said comparative spectral data to determine said concentration of said anionic species in said sample liquor.

2. A method as defined in claim 1 wherein said wavenumbers are selected from about 7,000 to 12,000 $cm^{-1}$.

3. A method as defined in claim 1 wherein said spectral data is transmittance spectra obtained by transmittance spectrophotometry.

4. A method as defined in claim 3 wherein said transmittance spectra is obtained by the reflectance of transmitted radiation with a reflectance cell.

5. A method as defined in claim 3 wherein said transmittance spectra is obtained from a direct coupled or a fibre-optic transmission probe.

6. A method as defined in claim 1 wherein said relationships between said spectral data of said sample and said comparative spectral data are obtained with a partial-least-squares multivariate calibration.

7. A method as defined in claim 1 wherein said path length is selected from 3–20 mm.

8. A method as defined in claim 7, wherein said path length is selected from 5–12 mm.

9. Method as defined in claim 1 wherein said solution further contains said organic species.

10. A method as defined in claim 1 for determining the concentration of said anionic species selected from $SO_4^=$ and $S_2O_3^=$.

11. A method as defined in claim 1 for determining the concentration of said polysulfide.

12. A method as defined in claim 1 for determining the concentration of said peroxide.

13. A method as defined in claim 1 for determining the concentration of said $ClO_3^-$.

14. A method for determining the concentration of hydrogen ion as defined in claim 1.

15. A method as defined in claim 1 wherein said solution contains $Cl^-$.

16. A method as defined in claim 1 wherein said aqueous sample solution is a pulp liquor selected from the group consisting of black liquor, white liquor and green liquor.

17. A method for controlling the operation of individual unit operations within a cellulosic pulp manufacturing process, which method comprises the steps of:

subjecting samples of process liquors containing at least $OH^-$, $CO_3^=$ and $HS^-$ anionic species and (ii) one or more components selected from the group consisting of solids, suspended fibers, suspended solids, gaseous bubbles, lignin, hemicellulose and cellulose degradation products, fatty acids and resinous acids to near infrared radiation at a wavelength region of wavenumbers from about 7,000 to 14,000 $cm^{-1}$ to produce measurements of said liquor;

recording the spectrum of different mixture solutions of synthetic and process liquors having known concentration parameters of at least one of said anionic species;

correlating by multivariate calibration the relationships between the spectra of the process liquor samples and the different mixture solutions of known concentration parameters so as to simultaneously determine concentration parameters in the process liquor samples; and adjusting the individual unit operations of the cellulosic pulp manufacturing process as required by controlling at least one process parameter to bring the final product of said unit operation to a desired value, wherein said final product is determined in part by concentration parameters in said process liquors, as determined by the near infrared measurement of said concentration parameters to a level of precision of about ±1 g/L species concentration.

18. A method as defined in claim 17 wherein said wavenumbers are selected from about 7,000 to 12,000 $cm^-$.

19. A method as defined in claim 18 wherein said controlled unit operation is a recovery process, wherein (i) residual cooking liquor from a digester is concentrated through a series of evaporators so as to produce strong black liquor, (ii) the strong black liquor is burned in a recovery furnace, (iii) the resulting smelt from the recovery furnace is fed to a smelt-dissolving tank to form green liquor, (iv) the green liquor is passed through a green liquor clarifier and made to enter a slaker, and (v) calcium oxide is added to the green liquor in the slaker so as to form a suspension which proceeds through a causticizer to a white liquor clarifier and subsequently fed to the digester.

20. A method as defined in claim 17, wherein said controlled unit operation is a pulp digestion process and wherein (i) wood chips and white liquor are fed into a digestion vessel, (ii) the wood chips are cooked at the elevated temperature and pressure for a desired length of time, (iii) the cooking liquor is withdrawn from various locations within the digestion vessel during the cooking period and optionally returned after subsequent heating with a heat exchanger, (iv) the resulting digested wood chips are discharged into a blow tank, and (v) the residual weak black cooking liquor is optionally returned to said digestion vessel.

21. A method as defined in claim 17, wherein said controlled unit operation is a brown-stock washing process and wherein (i) digested pulp from a blow tank is fed through a series of washing steps, (ii) the filtrate from each of the washing stages is separated from the pulp and optionally returned to another washing stage, and (iii) the cleaned pulp leaves the brown-stock washing process and enters a process selected from screening and/or bleaching process.

22. A method as defined in claim 17, wherein the near infrared measurements for determining the concentration parameters are carried out in the presence of dissolved sodium chloride.

23. A method as defined in claim 17, wherein the near infrared measurements for determining the concentration parameters are carried out in the presence of suspended solids.

24. A method as defined in claim 17, wherein the near infrared measurements for determining the concentration parameters are carried out in the presence of gaseous bubbles.

25. A method as defined in claim 17 wherein said process liquor further contains anionic organic species.

* * * * *